US006527774B2

(12) United States Patent
Lieberman

(10) Patent No.: US 6,527,774 B2
(45) Date of Patent: *Mar. 4, 2003

(54) APPARATUS FOR ATTACHING FRACTURED SECTIONS OF BONE

(75) Inventor: Isador H. Lieberman, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/835,334

(22) Filed: Apr. 16, 2001

(65) Prior Publication Data
US 2002/0055742 A1 May 9, 2002

Related U.S. Application Data

(63) Continuation-in-part of application No. 09/812,085, filed on Mar. 19, 2001, which is a continuation-in-part of application No. 09/781,847, filed on Feb. 14, 2001, which is a continuation-in-part of application No. 09/708,940, filed on Nov. 8, 2000, and a continuation-in-part of application No. 09/708,292, filed on Nov. 8, 2000, now Pat. No. 6,468,309.

(51) Int. Cl.⁷ .............................................. A61B 17/56
(52) U.S. Cl. ........................................ 606/61; 606/73
(58) Field of Search .............................. 606/61, 69, 71, 606/72, 73

(56) References Cited
U.S. PATENT DOCUMENTS 2,033,039 A 3/1936 Limpert ..................... 24/710.9

(List continued on next page.)

FOREIGN PATENT DOCUMENTS

| EP | 0374088 A1 | 6/1990 |
| EP | 0663184 A1 | 7/1995 |
| FR | 2299548 | 8/1976 |
| SU | 1071297 A | 2/1984 |
| WO | WO 0224087 A1 | 3/2002 |

OTHER PUBLICATIONS

An article entitled "Anterior Vertebral Body Screw Pullout Testing, A Comparison of Zielke, Kaneda, Universal Spine System with Pullout–Resistant Nut", by Isador H. Lieberman et al., reprinted from Spine, vol. 23, No. 8, Apr. 15, 1998.

(List continued on next page.)

Primary Examiner—John J. Wilson
(74) Attorney, Agent, or Firm—Tarolli, Sundheim, Covell & Tummino L.L.P.

(57) ABSTRACT

An apparatus (10) for attaching a first section (17) of a bone (12) to a second section (18) of the bone. The second section (18) is separated from the first section (17) by a fracture (14). The apparatus (10) comprises a bone screw (20) having a platform (24) and at least two helical spikes (50 and 52) for embedding into at least one of the first and second sections (17 and 18). The helical spikes (50 and 52) project tangentially from the platform (24). The helical spikes (50 and 58) have a tip portion (58) which penetrates into the bone (12) as the platform (24) is rotated. The bone screw (20) has a first condition in which a first portion (58) of the bone screw extends into one of the first and second sections (17 and 18) and a second condition in which a second portion (24) of the bone screw extends into the other of the first and second sections to compress the first and second sections together.

30 Claims, 13 Drawing Sheets

U.S. PATENT DOCUMENTS

| | | | |
|---|---|---|---|
| 4,762,453 A | 8/1988 | DeCaro | 411/383 |
| 4,854,311 A | 8/1989 | Steffee | 606/66 |
| 5,055,104 A | 10/1991 | Ray | 606/61 |
| 5,116,336 A | 5/1992 | Frigg | 606/65 |
| 5,246,443 A * | 9/1993 | Mai | 606/78 |
| 5,263,953 A | 11/1993 | Bagby | 606/53 |
| 5,290,289 A | 3/1994 | Sanders et al. | 606/61 |
| 5,534,031 A | 7/1996 | Matsuzaki et al. | 623/17 |
| 5,582,616 A | 12/1996 | Bolduc et al. | 606/143 |
| 5,626,613 A | 5/1997 | Schmieding | 606/232 |
| 5,662,683 A | 9/1997 | Kay | 606/232 |
| 5,728,116 A | 3/1998 | Rosenman | 606/151 |
| 5,791,899 A | 8/1998 | Sachdeva et al. | 433/173 |
| 5,810,851 A | 9/1998 | Yoon | 606/148 |
| 5,824,008 A | 10/1998 | Bolduc et al. | 606/43 |
| 5,904,696 A | 5/1999 | Rosenman | 606/151 |
| 6,036,701 A | 3/2000 | Rosenman | 606/151 |
| 6,117,162 A | 9/2000 | Schmieding et al. | 606/232 |
| 6,296,656 B1 | 10/2001 | Bolduc et al. | 606/213 |

OTHER PUBLICATIONS

An excerpt from *The Application of Shape Memory Alloys in Medicine*; Author: I.P. Lipscomb, 1996; Contents; Forward; Preface; Chapter 1 "Introduction to Shape Memory Alloys (SMAs)".

An excerpt from *The Application of Shape Memory Alloys in Medicine*; Author: I.P. Lipscomb, 1996; Chapter 2 entitled "Characteristics of Shape Memory Alloys in Medical Applications".

An excerpt from *The Application of Shape Memory Alloys in Medicine*; Author: I.P. Lipscomb, 1996; Chapter 5 "Present and Future Orthopaedic Applications".

\* cited by examiner

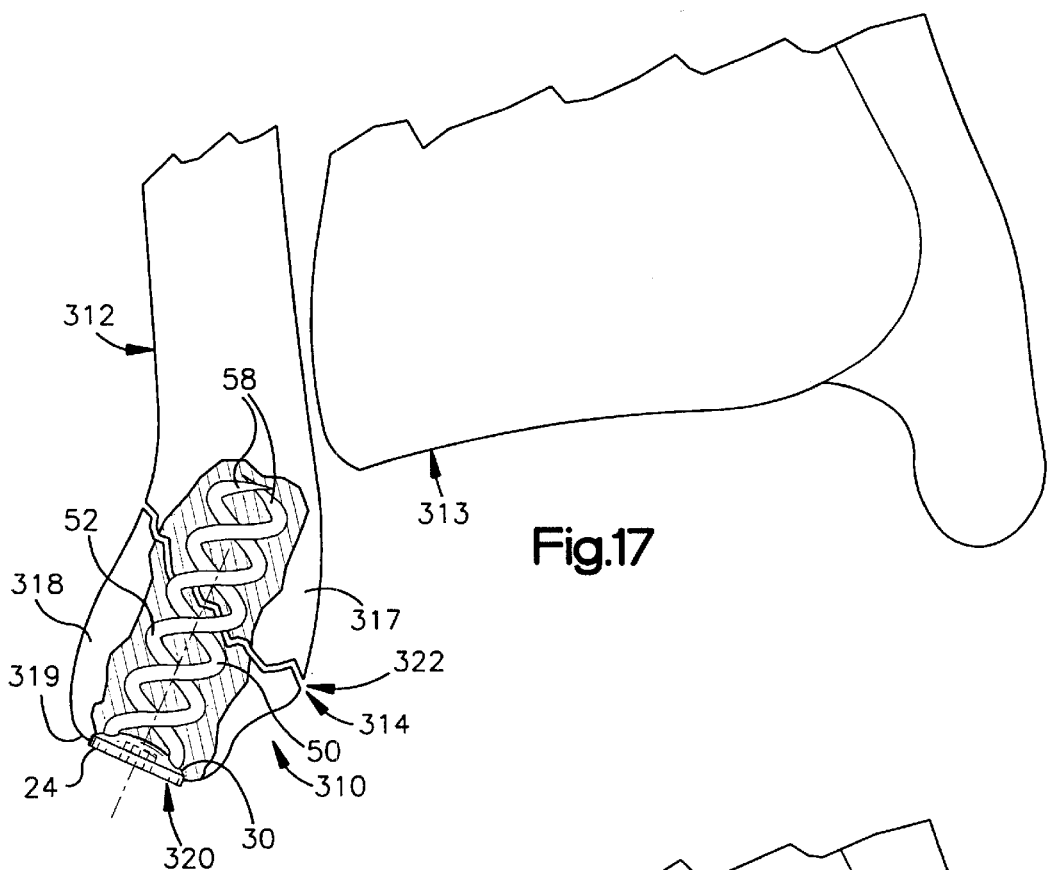
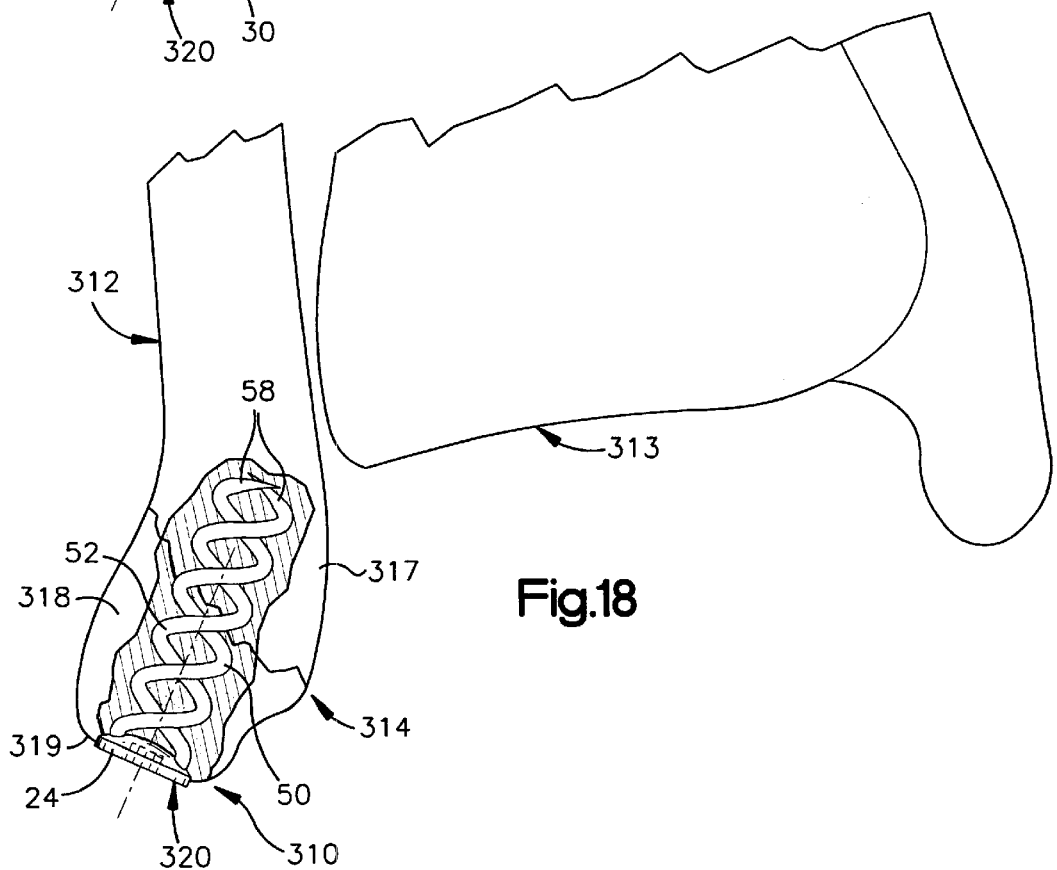

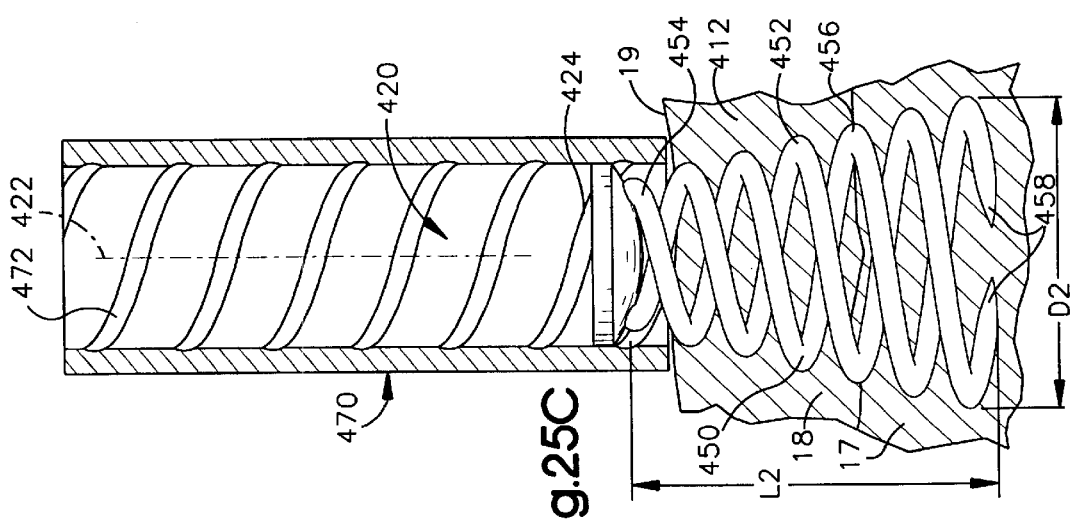
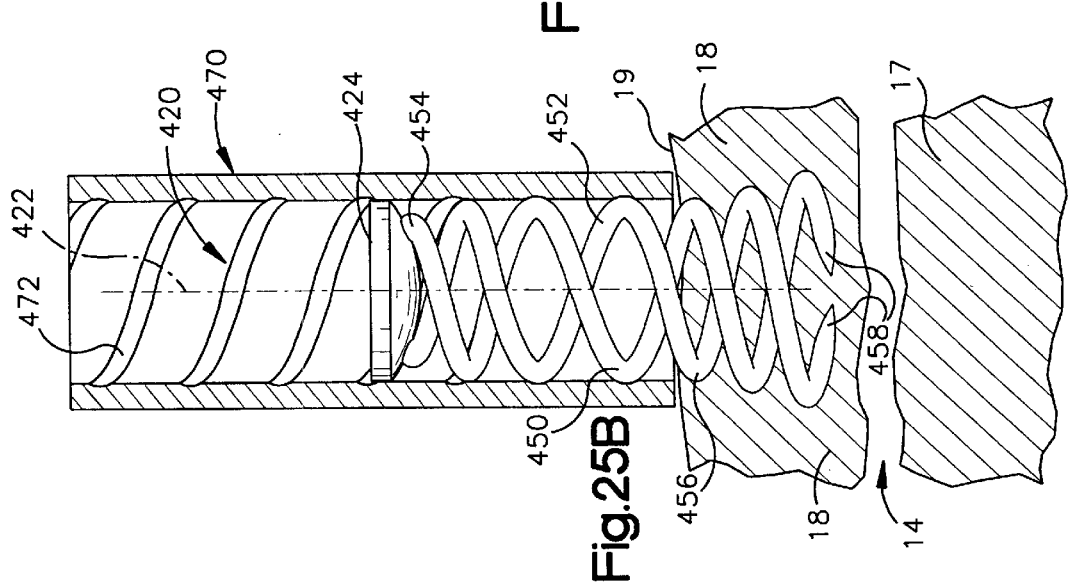
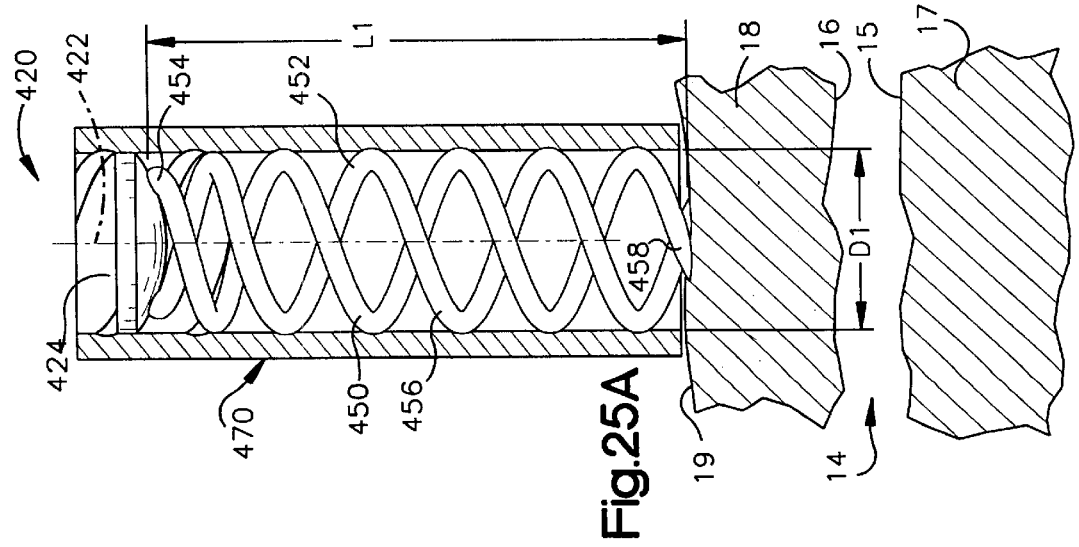

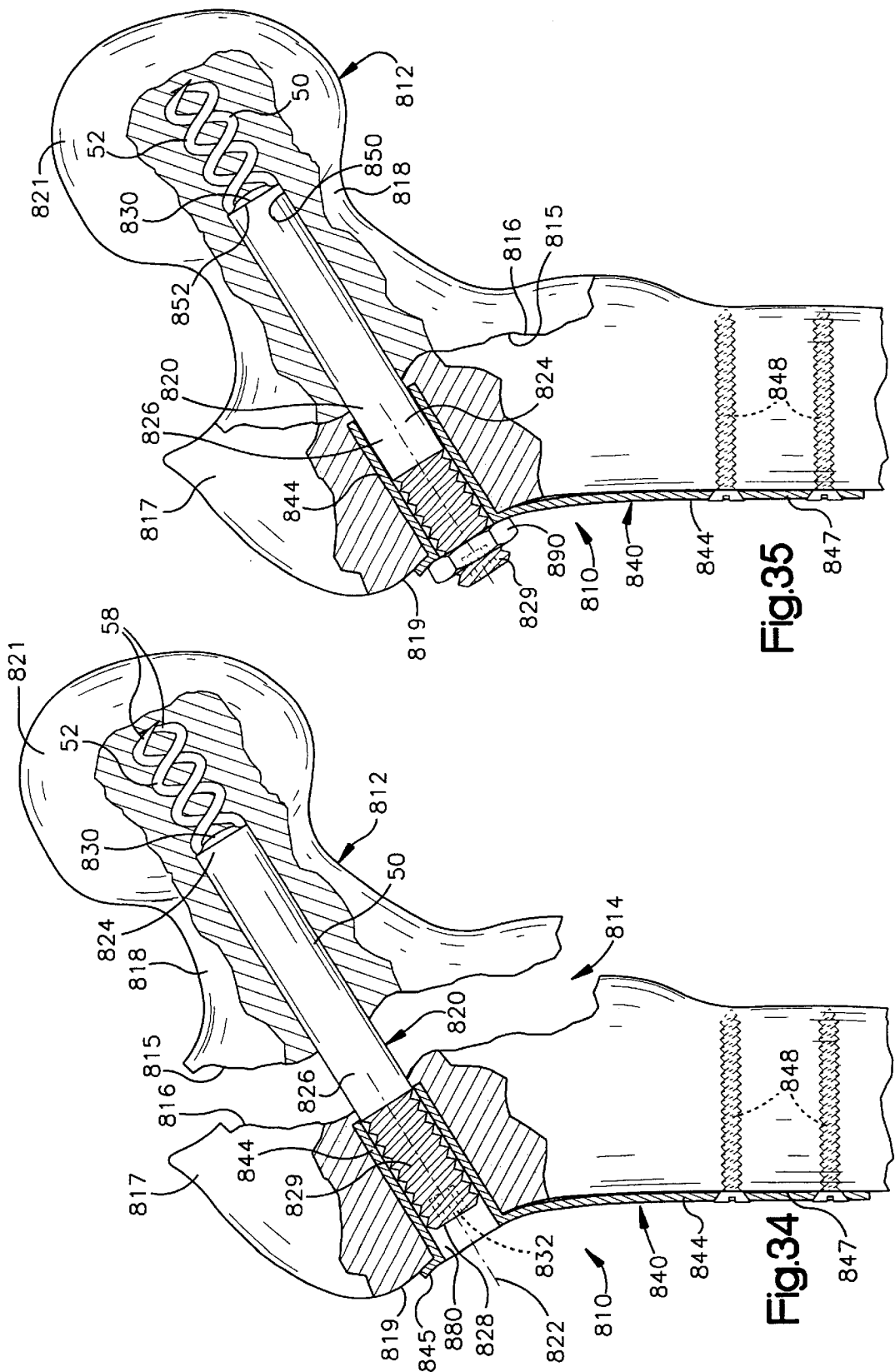

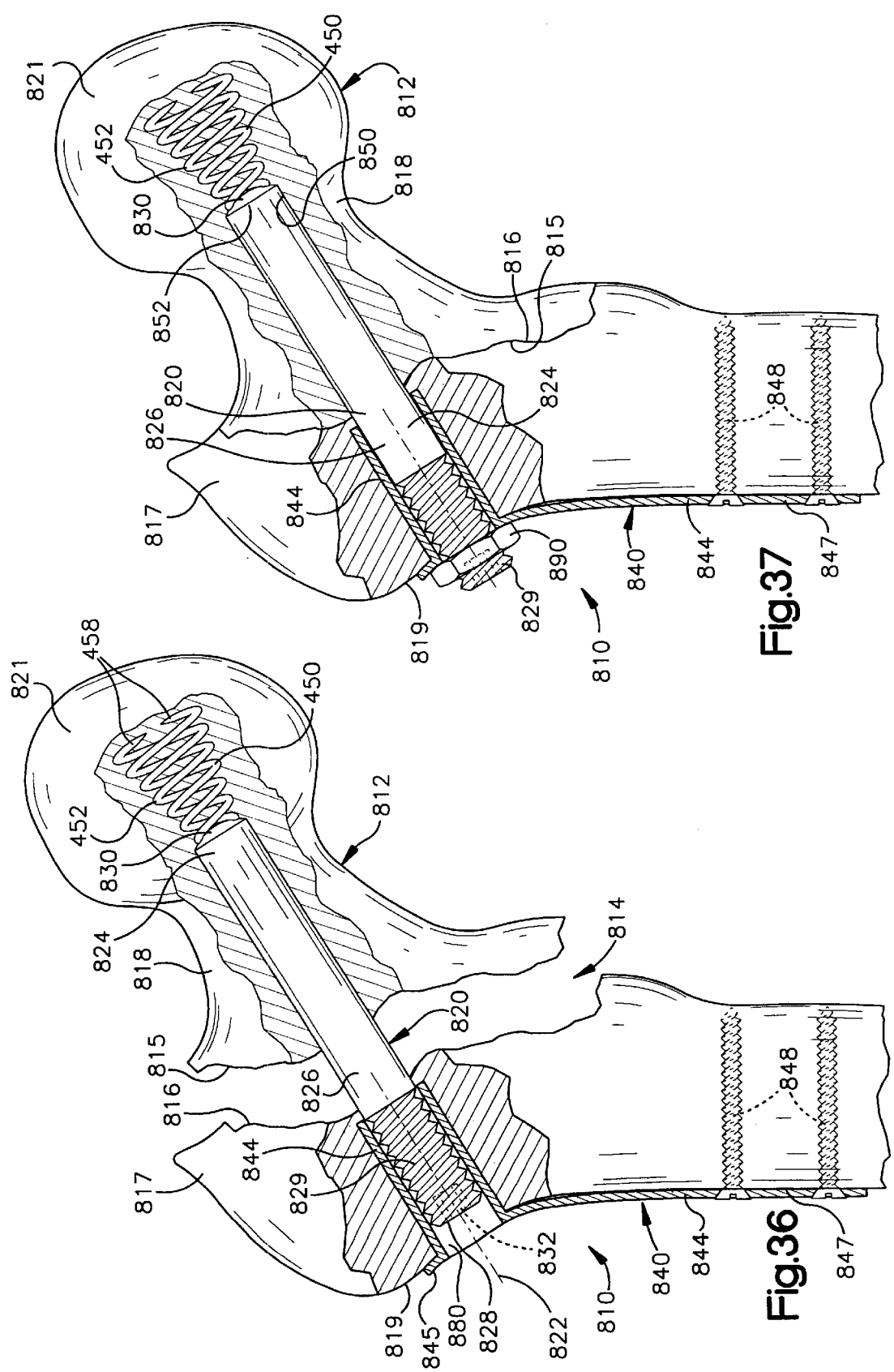

APPARATUS FOR ATTACHING FRACTURED SECTIONS OF BONE

RELATED APPLICATIONS

This application is a continuation-in-part of co-pending U.S. patent application Ser. No. 09/812,085, filed Mar. 19, 2001, which is itself a continuation-in-part of co-pending U.S. patent application Ser. No. 09/781,847, filed Feb. 14, 2001, which is itself a continuation-in-part of co-pending U.S. patent application Ser. Nos. 09/708,940 and 09/708,292, both which were filed Nov. 8, 2000 now U.S. Pat. No. 6,468,309. The entire subject matter of the aforementioned four co-pending applications is incorporated herein by reference.

TECHNICAL FIELD

The present invention is directed to an apparatus for attaching fractured sections of bone in a patient's body, and is particularly directed to an apparatus that, when implanted, is resistant to toggling in the bone and to being pulled from the bone. The fixation apparatus prevents relative rotation of the fractured sections of bone without damaging the sections.

BACKGROUND OF THE INVENTION

Bone screws are used in the medical field for a variety of purposes. Typical uses for bone screws, also referred as anchors, include treating a bone fracture by attaching fractured sections, attaching a corrective device to parts of a fractured bone in an area adjacent to the fracture, and attaching soft tissue, such as a ligament or tendon, to bone.

Most known bone screws use a conventional screw design, i.e. a solid shank, with one or more external thread convolutions. The solid shank and external threads of the conventional bone screws can cause the bone screws to displace and/or destroy an undesirably large amount of bone when implanted. Typically, implantation of a bone screw into bone involves drilling a hole, tapping the hole, and then inserting the screw. In the case of a fracture, such drilling and tapping can further fragment the fractured sections of bone. Such conventional bone screws can also require a large amount of torque to implant the screw into a bone or through a fractured segment of bone. Further, the resistance of the conventional screw to being pulled axially from the bone is dependent upon the surface area of the bone that interfaces with the screw threads.

It is also known to use a corkscrew-style helical spike as a bone screw or tissue anchor. The known corkscrew-style tissue anchors, when implanted, displace less bone than the conventional bone screws, but are generally not able to withstand high tensile loads without structural failure. European Patent No. 0 374 088 A1 discloses a bone screw having a twin-corkscrew design. In this twin-corkscrew design, which is formed by drilling a passage up through a screw having a solid shank and then machining out the material between the two corkscrews, the junction of the corkscrews with the shank is unlikely to be capable of structurally withstanding high tensile loads and repetitive fatigue loads. This structural weakness in the design of the screw in the EP 0 374 088 document is further compounded by the corkscrews having a larger overall diameter than the head of the screw where torque is applied.

Many of the known bone screws, such as those described above, can be susceptible to toggling in the bone and can also pull out of the bone due to the substantial forces on the screws from human body movement and muscle memory. In order to achieve a high pull-out resistance, it is common to use additional screws, which results in an undesirably large amount of bone being displaced. In order to achieve a high pull-out resistance, it is also known to thread a bone screw all of the way through a bone and place a nut on the opposite side. However, use of such a nut increases the complexity of the surgical procedure.

Hence, it is desirable to provide an apparatus for implantation into a bone in a patient's body in a minimally invasive or endoscopic procedure with a reduced amount of insertion torque required. The desirable apparatus, when implanted, would be highly resistant to toggling in the bone and to being pulled out of the bone despite the substantial forces on the apparatus from human body movement and muscle memory. Further, the desirable apparatus would be able to compress fractured sections of bone together to prevent relative rotation of the fractured sections and permit healing of the fracture without causing any further damage to the fractured sections.

SUMMARY OF THE INVENTION

The present invention is an apparatus for attaching a first section of a bone to a second section of the bone. The second section is separated from the first section by a fracture of the bone. The apparatus comprises a bone screw having a platform for drivingly rotating the bone screw and at least two helical spikes for embedding into at least one of the first and second sections of the bone upon rotation of the platform. The at least two helical spikes project tangentially from the platform and extend around a longitudinal axis. The at least two helical spikes have a tip portion at a distal end which penetrates into the bone as the platform is rotated. The bone screw has a first condition in which a first portion of the bone screw extends into one of the first and second sections of the bone. The bone screw further has a second condition in which a second portion of the bone screw extends into the other of the first and second sections of the bone to compress the first and second sections together so that the fracture of the bone can heal. The at least two helical spikes, when embedded into at least one of the first and second sections of the bone, are resistant to toggling in the bone and to being pulled axially from the bone.

In accordance with another feature of the present invention, an apparatus is provided for attaching a first section of a bone to a second section of the bone. The second section is separated from the first section by a fracture of the bone. The apparatus comprises a bone screw for extending between the first and second sections of the bone and for attaching the first section to the second section. The bone screw has a platform for drivingly rotating the bone screw. The bone screw further has at least two helical spikes for embedding into both of the first and second sections of the bone upon rotation of the platform. The at least two helical spikes project tangentially from the platform and extend around a longitudinal axis. The at least two helical spikes have a tip portion at a distal end which penetrates into the bone as the platform is rotated. The bone screw has a first condition in which the at least two helical spikes are embedded into one of the first and second sections of the bone. The bone screw further has a second condition in which the at least two helical spikes are embedded into both of the first and second sections of the bone to compress the first and second sections together so that the fracture of the bone can heal. The bone screw is movable from the first condition to the second condition by rotation of the platform. The at least two helical spikes of the bone screw, when embedded into the first and second sections of the bone, are resistant to toggling in the bone and to being pulled axially from the bone.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 17 is a side view illustrating an apparatus for attaching fractured sections of bone in accordance with a fourth embodiment of the present invention, the apparatus being shown in a first condition;

FIG. 18 is a view similar to FIG. 17 illustrating the apparatus in a second condition;

FIG. 25A is a side view, partially in section, illustrating the apparatus of FIG. 21 prior to implantation into the bone;

FIG. 25B is a view similar to FIG. 25A further illustrating the first condition of the apparatus shown in FIG. 20;

FIG. 25C is a view similar to FIG. 25A further illustrating the second condition of the apparatus shown in FIG. 21;

FIG. 34 is a schematic view illustrating an apparatus for attaching fractured sections of bone in accordance with a ninth embodiment of the present invention, the apparatus being shown in a first condition;

FIG. 35 is a view similar to FIG. 34 illustrating the apparatus in a second condition;

FIG. 36 is a schematic view illustrating an apparatus for attaching fractured sections of bone in accordance with a tenth embodiment of the present invention, the apparatus being shown in a first condition; and FIG. 37 is a view similar to FIG. 36 illustrating the apparatus in a second condition.

DESCRIPTION OF PREFERRED EMBODIMENTS

Figure 1:
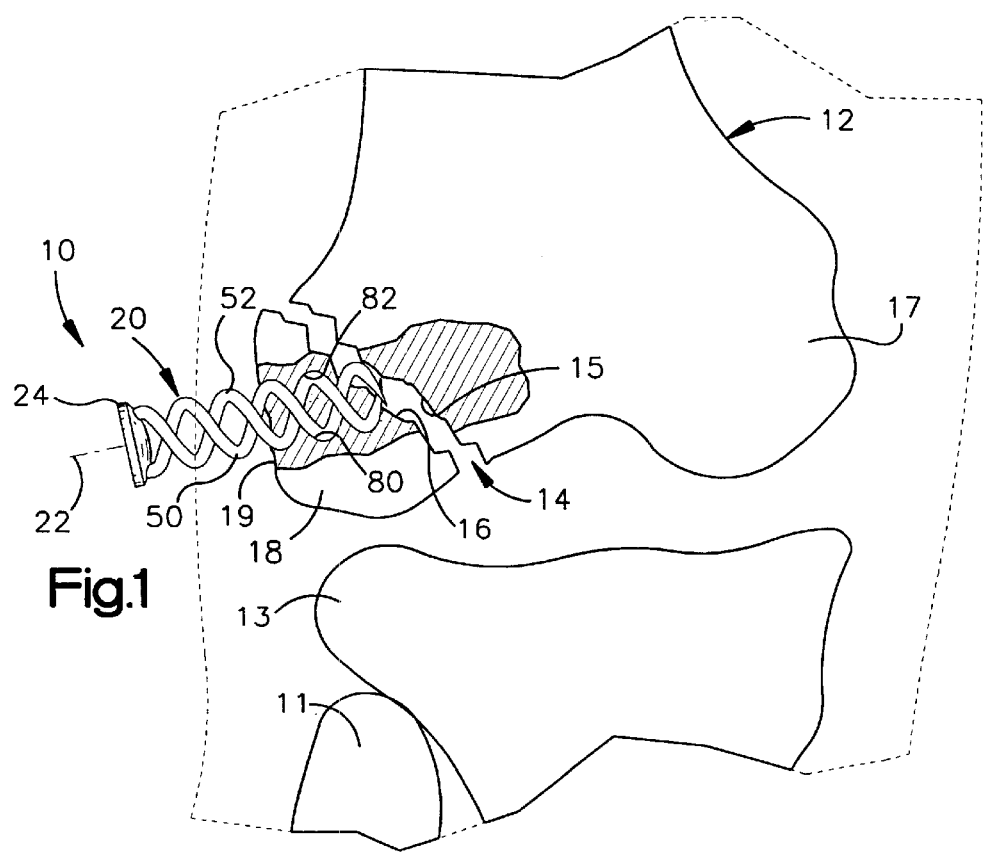
FIG. 1 is a schematic view of an apparatus for attaching fractured sections of bone in accordance with the present invention, the apparatus being shown in a first condition.

The present invention is directed to an apparatus for attaching fractured sections of bone, and is particularly directed to an apparatus that, when implanted, is resistant to toggling in the bone and to being pulled from the bone. As representative of the present invention, FIG. 1 illustrates an apparatus 10 partially implanted in the distal end of a femur 12, adjacent the proximal ends of a fibula 11 and a tibia 13. The distal end of the femur 12 has a fracture 14 defined by opposing first and second edges 15 and 16. The fracture 14 divides the femur 12 into a main body section 17 and a fractured section 18. The main body section 17 includes the first edge 15. The fractured section 18 includes the second edge 16 and an outer surface 19.

The apparatus 10 comprises a bone screw 20 made from a biocompatible material, such as titanium or stainless steel. It is contemplated that the biocompatible material used for the bone screw 20 could be polymeric or composite (i.e., carbon fiber or other biologic composite) in nature. It is further contemplated that the biocompatible material used to make the bone screw 20 could also be biodegradable.

Figure 3:
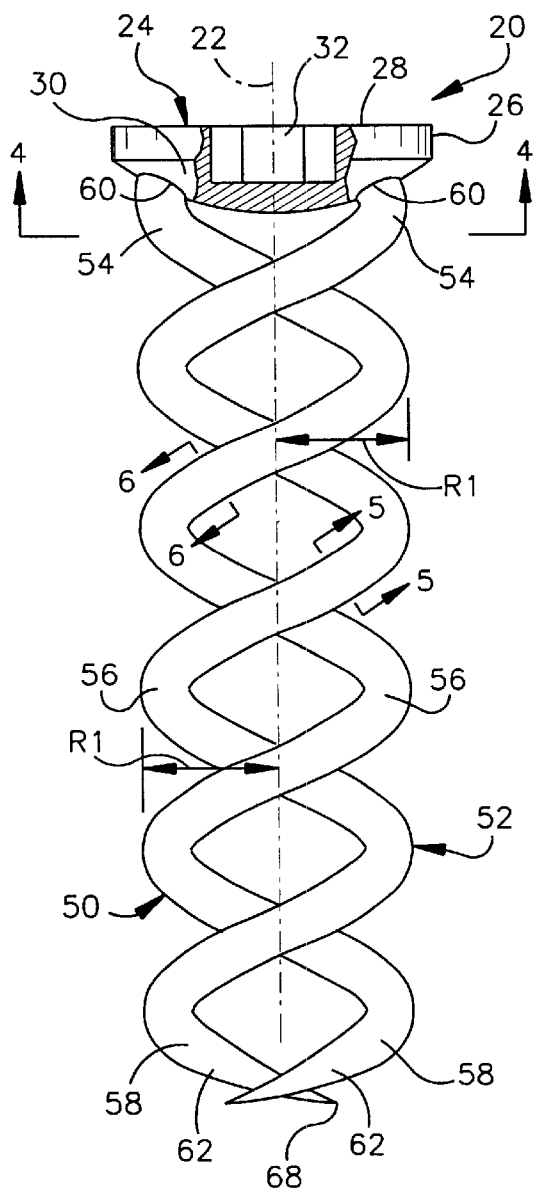
FIG. 3 is a side view of the apparatus of FIG. 1.

The bone screw 20 is centered about a longitudinal axis 22 (FIG. 3). The bone screw 20 includes a platform 24 having a cylindrical outer surface 26 extending between oppositely disposed first and second end surfaces 28 and 30 of the platform. The first end surface 28 is planar, while the second end surface 30 has a convex shape that is complimentary to the shape of the outer surface 19 of the fractured section 18 of the femur 12. It should be understood that the second end surface 30 could be any shape that is complimentary to the outer surface 19 of the fractured section 18.

The second end surface 30 of the platform 24 may include barbs (not shown) or other suitable structure for engaging the side surface 14 of the femur 12. Further the second end surface 30 of the platform 24 may also be porous, pitted, or have a biocompatible surface coating to assist with fixation of the bone screw 20 to the fractured section 18 of the femur 12.

The platform 24 further includes a hexagonal slot 32 that extends axially from the first end surface 28 toward the second end surface 30 of the platform. The hexagonal slot 32 is designed to receive a driver (not shown) for rotating the bone screw 20.

Figure 5:
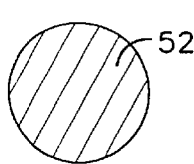
FIG. 5 is a sectional view taken along 5—5 in FIG. 3.
Figure 5A:
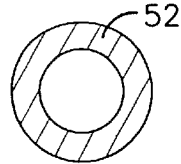
FIG. 5A is a sectional view similar to FIG. 5 illustrating an alternate configuration.
Figure 6:
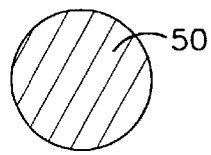
FIG. 6 is a sectional view taken along 6—6 in FIG. 3.
Figure 6A:
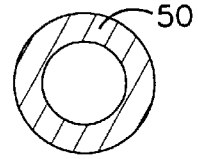
FIG. 6A is a sectional view similar to FIG. 6 illustrating an alternate configuration.
Figure 8:
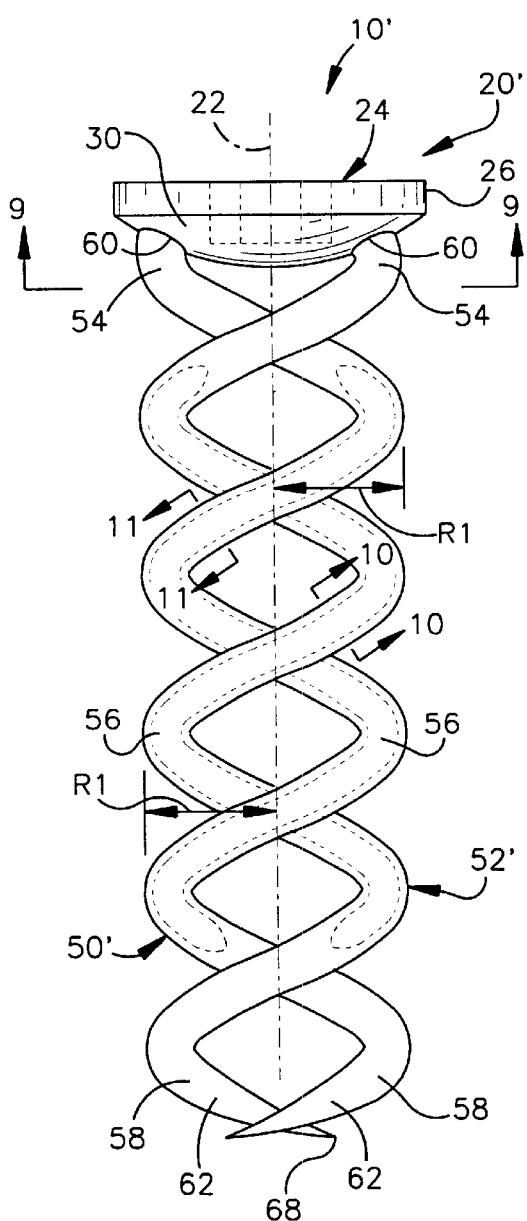
FIG. 8 is a side view illustrating an apparatus for attaching fractured sections of bone in accordance with a second embodiment of the present invention.
Figure 9:
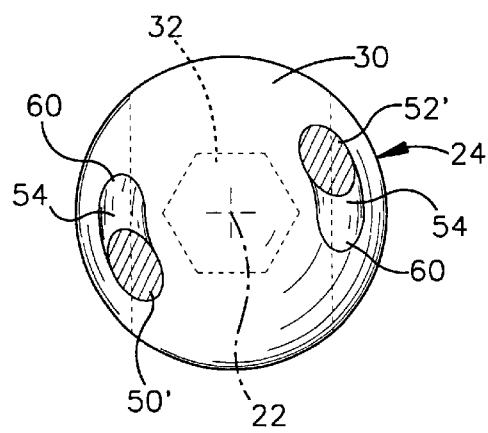
FIG. 9 is a sectional view taken along line 9—9 in FIG. 8.
Figure 10:
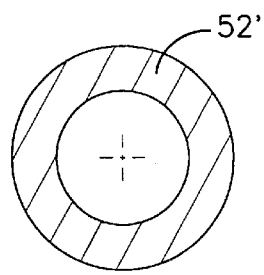
FIG. 10 is a sectional view taken along 10—10 in FIG. 8.
Figure 11:
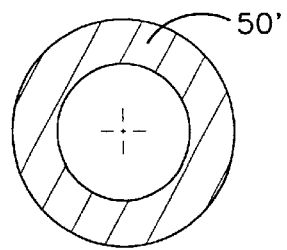
FIG. 11 is a sectional view taken along line 11—11 in FIG. 8.

First and second helical spikes 50 and 52 project tangentially from the second end surface 30 of the platform 24. The helical spikes 50 and 52 resemble a pair of intertwined corkscrews. As shown in FIGS. 5 and 6, each of the helical spikes 50 and 52 has a solid cross-section. Alternatively, each of the helical spikes 50 and 52 could have a tubular cross-section, as illustrated in FIGS. 5A and 6A, which provides a means for matching the modulus of elasticity of the bone. It is contemplated that, with a tubular cross-section, the wall thickness can be varied/selected to match the modulus of elasticity of the bone, which can improve fixation strength and load-sharing characteristics of the bone screw 20 and the bone.

According to the embodiment illustrated in FIGS. 1–6, the first and second helical spikes 50 and 52 extend around the axis 22. The spikes 50 and 52 extend in a helical pattern about the axis 22 at the same, constant overall radius R1 (FIG. 3). It is contemplated, however, that the first and second helical spikes 50 and 52 could extend about the axis 22 at different radiuses. Further, it is contemplated that the radius of one or both of the first and second helical spikes 50 and 52 could increase or decrease as the helical spikes extend away from the platform 24. In order for the bone screw 20 to be implanted endoscopically through a typical cannula (not shown), the platform 24 and the helical spikes 50 and 52 should be less than 20 mm in overall diameter. It should be understood that the bone screw 20 could have an overall diameter that is greater than 20mm for certain applications, and that the bone screw could be also implanted in an open surgical procedure.

In the illustrated embodiment of FIGS. 1–6, the first and second helical spikes 50 and 52 have the same axial length, and also have the same cross-sectional shape. It is contemplated, however, that the first and second helical spikes 50 and 52 could have different axial lengths. Further, it is contemplated that the helical spikes 50 and 52 could have a different cross-sectional shape, such as an oval shape.

It also contemplated that the first and second helical spikes 50 and 52 could have different outer diameters (i.e., one spike being thicker than the other spike). Finally, it is contemplated that the helical spikes 50 and 52 should have the same pitch, and that the pitch of the helical spikes would be selected based on the specific surgical application and quality of the bone in which the bone screw 20 is to be implanted.

Each of the first and second helical spikes 50 and 52 can be divided into three portions: a connecting portion 54, an intermediate portion 56, and a tip portion 58. The connecting portion 54 of each of the helical spikes 50 and 52 is located at a proximal end 60 that adjoins the second end surface 30 of the platform 24. The connecting portion 54 may include barbs (not shown) for resisting pull-out of the helical spikes 50 and 52 from the femur 12. According to one method for manufacturing the bone screw 20, the connecting portion 54 of each of the helical spikes 50 and 52 is fixedly attached to the platform 24 by inserting, in a tangential direction, the proximal ends 60 of the helical spikes into openings (not shown) in the second end surface 30 and welding the connecting portions 54 to the platform. The inserted proximal ends 60 of the helical spikes 50 and 52 help to reduce bending stresses on the helical spikes under tensile or shear loads.

Alternatively, the helical spikes 50 and 52 may be formed integrally with the platform 24, such as by casting the bone screw 20. If the bone screw 20 is cast, it is contemplated that a fillet (not shown) may be added at the junction of the helical spikes 50 and 52 and the platform 24 to strengthen the junction and minimize stress concentrations at the connecting portions 54. The fillet at the junction of the helical spikes 50 and 52 and the platform 24 also helps to reduce bending stresses in the connection portions 54 of the helical spikes under tensile or shear loads.

Figure 4:
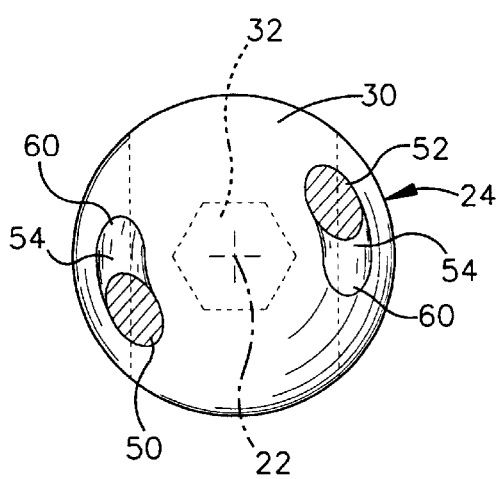
FIG. 4 is a sectional view taken along 4—4 in FIG. 3.

As best seen in FIG. 4, the connecting portions 54 at the proximal ends 60 of the first and second helical spikes 50 and 52 are spaced 180° apart about the axis 22 to balance the bone screw 20 and evenly distribute loads on the helical spikes. The tip portion 58 of each of the helical spikes 50 and 52 is located at a distal end 62 of the helical spikes. The intermediate portion 56 of each of the helical spikes 50 and 52 extends between the tip portion 58 and the connecting portion 54. The intermediate portion 56 and the tip portion 58 of each of the helical spikes 50 and 52 have an outer diameter that is less than or equal to the outer diameter of the connecting portions 54. If the outer diameter of the intermediate portion 56 and the tip portion 58 is less than the outer diameter of the connecting portion 54 of each of the helical spikes 50 and 52, the increased thickness of the connecting portions will help to provide the bone screw 20 with increased tensile strength at the junction of the helical spikes and the platform 24.

Figure 7:
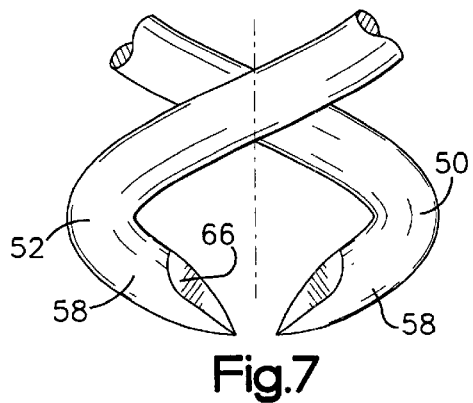
FIG. 7 illustrates an alternate configuration for an end portion of the apparatus of FIG. 1.

The tip portion 58 of each of the helical spikes 50 and 52 illustrated in FIGS. 1–6 has an elongated conical shape with a sharp pointed tip 68 for penetrating into the femur 12 as the platform 24 of the bone screw 20 is rotated in a clockwise direction. FIG. 7 illustrates an alternative, self-tapping configuration for the tip portions 58 which includes a planar surface 66 for driving into the femur 12, in the same manner that a wood chisel turned upside-down drives into wood, as the platform 24 is rotated. It is contemplated that the tip portions 58 could also have a pyramid shape (not shown), similar to the tip of a nail.

Although the outer surfaces of the helical spikes 50 and 52 are shown as being smooth in FIGS. 1–6, it is contemplated that the outer surfaces may instead be porous, pitted, or have a biocompatible coating to assist with fixation of the bone screw 20 to the femur 12.

It is further contemplated that the tip portions 58 of the helical spikes 50 and 52 could be covered with tip protectors (not shown) to prevent accidental sticks to surgical staff and accidental damage to tissue surrounding the femur. Such tip protectors could be made of a bio-absorbable material, such as polylactic acid, or non-bio-absorbable material, such as medical grade silicon. The tip protectors would be manually removed or pushed-off during implantation of the bone screw 20.

To use the bone screw 20 to attach the fractured section 18 to the main body section 17 of the femur 12, a tool (not shown) is used to punch two holes (not shown) in the outer surface 19 of the fractured section. The holes are punched in locations that correspond to the spacing of the tip portions 58 of the helical spikes 50 and 52 on the bone screw 20. It should be noted that one or both of the configurations of the tip portions 58 illustrated in FIGS. 1–7 may be able to punch through the outer surface 19 upon rotation of the bone screw 20, thus eliminating the need for the aforementioned tool to punch holes in the outer surface.

The tip portions 58 are then placed in the holes in the fractured section 18 and a rotatable driver (not shown) is inserted into the slot 32 in the platform 24. The driver is then rotated, causing the bone screw 20 to rotate as well. It is contemplated that a cylindrical sleeve (not shown) may be placed around the intermediate portions 56 and the connecting portions 54 of the helical spikes 50 and 52 to prevent the helical spikes from deforming radially outward during the initial rotation of the bone screw 20.

Rotation of the bone screw 20 screws the helical spikes 50 and 52 into the cancellous bone of the fractured section 18 of the femur 12. The tangentially-oriented connection between the connecting portions 54 of the helical spikes 50 and 52 and the platform 24 minimizes bending loads on the connecting portions during rotation of the bone screw 20. Further, the tangentially-oriented connection ensures that the force vector resulting from torque and axial force applied by the driver to platform 24 is transmitted along the helical centerline (not shown) of each of the helical spikes 50 and 52.

As the bone screw 20 is rotated, the tip portion 58 of the first helical spike 50 penetrates the cancellous bone and cuts a first helical tunnel 80 (FIG. 1) through the fractured section 18 of the femur 12. Simultaneously, the tip portion 58 of the second helical spike 52 penetrates the cancellous bone of the femur 12 and cuts a second helical tunnel 82. The first and second helical tunnels 80 and 82 are shaped like the helical spikes 50 and 52, respectively.

Continued rotation of the bone screw 20 embeds the helical spikes 50 and 52 deeper into the cancellous bone of the fractured section 18 until the tip portions 58 of the helical spikes project through the first edge 15 on the fractured section. With the second edge 16 on the fractured section 18 held firmly against the first edge 15 on the main body section 17, the platform 24 is further rotated, causing the tip portions 58 of the helical spikes 50 and 52 to penetrate through the first edge and into the main body section of the femur 12.

Figure 2:
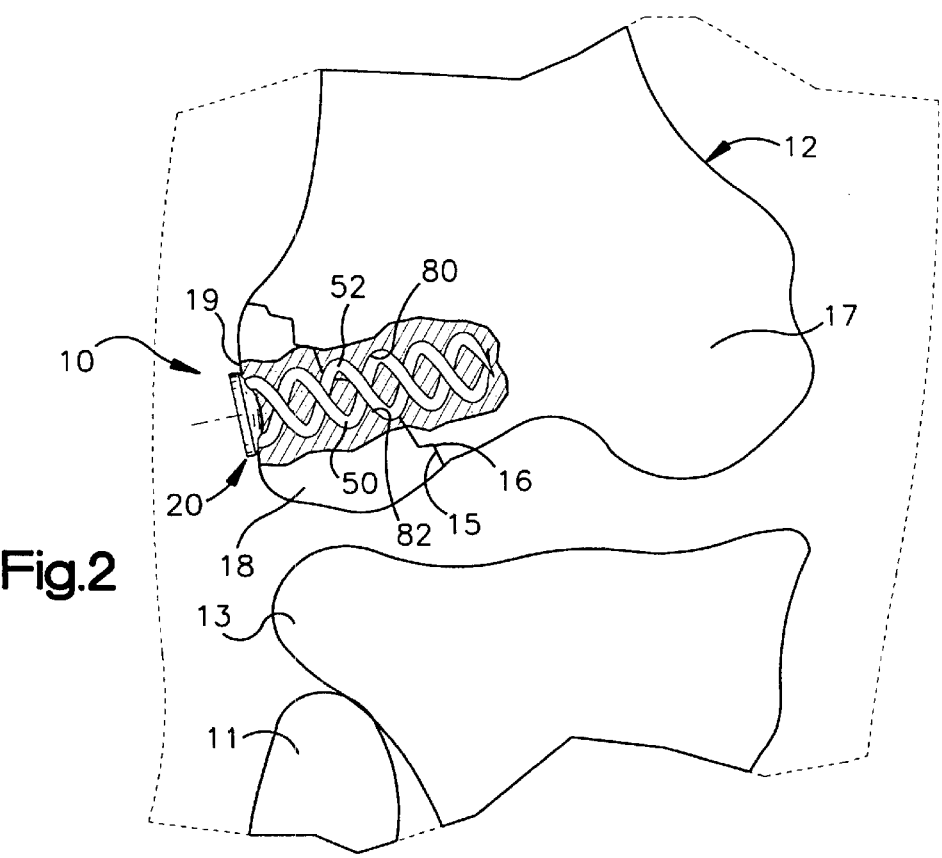
FIG. 2 is a view similar to FIG. 1 illustrating the apparatus in a second condition.

As the bone screw is rotated further, the first and second helical spikes 50 and 52 cut into the main body section 17 and extend the first and second helical tunnels 80 and 82, respectively, into the main body section. The bone screw 20 is rotated until the second end surface 30 on the platform 24 seats tightly against the outer surface 19 of the fractured section 18 as shown in FIG. 2. As the second end surface 30 on the platform 24 seats tightly against the outer surface 19, the first and second edges 15 and 16 are moved into engagement with each other. With the fractured section 18 and the main body section 17 of the femur 12 attached to each other by the bone screw 20, the fracture 14 in the femur can heal over time.

It should be noted that in the event that the bone screw 20 to be implanted is made from a polymeric or composite material, it may be necessary to use a metal bone screw as a "tap" to cut the helical tunnels 80 and 82 in the sections 17 and 18 of the femur 12 prior to implantation of the polymeric or composite bone screw.

Because the helical spikes 50 and 52 of the bone screw 20 displace much less of the cancellous bone in the main body section 17 and the fractured section 18 of the femur 12 during implantation than a conventional solid shank bone screw, much less torque is required to implant the bone screw in the femur than is required by a conventional bone screw. Further, because the helical spikes 50 and 52 displace only a small amount of bone, the helical spikes do not create a core defect that could lead to bone deformation or failure, such as the helical spikes pulling out of the bone.

When implanted, a bone screw can be subjected to substantial forces caused by human body movement and muscle memory. In some cases, these forces can tend to pull the known screws used in such an application out of the bone or can cause the screws to toggle in the bone. However, when embedded in a bone such as the femur 12 shown in FIG. 2, the helical spikes 50 and 52 provide the bone screw with a high resistance to pull-out forces. Further, the helical spikes 50 and 52, and their tangential connection with the platform 24, provide the bone screw 20 with a high resistance to toggling in the bone. Thus, the bone screw 20 provides an effective means for compressing the fractured sections 17 and 18 of the femur 12 together to prevent relative rotation of the fractured sections and permit healing of the fracture 14 without causing any further damage to the fractured sections.

FIGS. 8–11 illustrate an apparatus 10' for attaching fractured sections of bone in accordance with a second embodiment of the present invention. In the second embodiment of FIGS. 8–11, reference numbers that are the same as those used in the first embodiment of FIGS. 1–6 designate parts that are the same as parts in the first embodiment.

According to the second embodiment, the apparatus 10' comprises a bone screw 20' having helical spikes 50' and 52'. FIGS. 8–11 illustrate the connecting portions 54 and the tip portions 58 of the helical spikes 50' and 52' having a solid cross-section, while the intermediate portions 56 have a tubular cross-section. Such a modified configuration of the bone screw 20' provides means for matching the modulus of elasticity of the bone, which allows the surgeon to select a particular configuration for the bone screw based on the specific surgical application and quality of the bone in which the bone screw is to be implanted.

FIGS. 12–16 illustrate an apparatus 210 for attaching fractured sections of bone constructed in accordance with a third embodiment of the present invention. In the third embodiment of FIGS. 12–16, reference numbers that are the same as those used in the first embodiment of FIGS. 1–6 designate parts that are the same as parts in the first embodiment.

Figures 14, 14A:
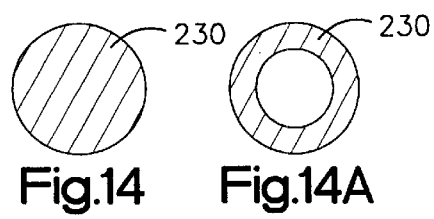
FIG. 14 is a sectional view taken along line 14—14 in FIG. 12.
FIG. 14A is a sectional view similar to FIG. 14 illustrating an alternate configuration.
Figures 15, 15A:
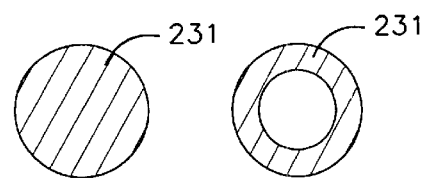
FIG. 15 is a sectional view taken along 15—15 in FIG. 12.
FIG. 15A is a sectional view similar to FIG. 15 illustrating an alternate configuration.
Figures 16, 16A:
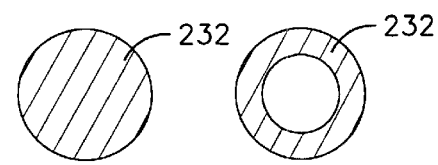
FIG. 16 is a sectional view taken along 16—16 in FIG. 12.
FIG. 16A is a sectional view similar to FIG. 16 illustrating an alternate configuration.

According to the third embodiment, the apparatus 210 comprises a bone screw 220 having three helical spikes 230, 231, and 232 projecting tangentially from the second end surface 30 of the platform 24. As shown in FIGS. 14–16, each of the helical spikes 230–232 has a solid cross-section. Alternatively, each of the helical spikes 230–232 could have a tubular cross-section, as is illustrated in FIGS. 14A–16A, which provides a means for matching the modulus of elasticity of the bone.

Figure 12:
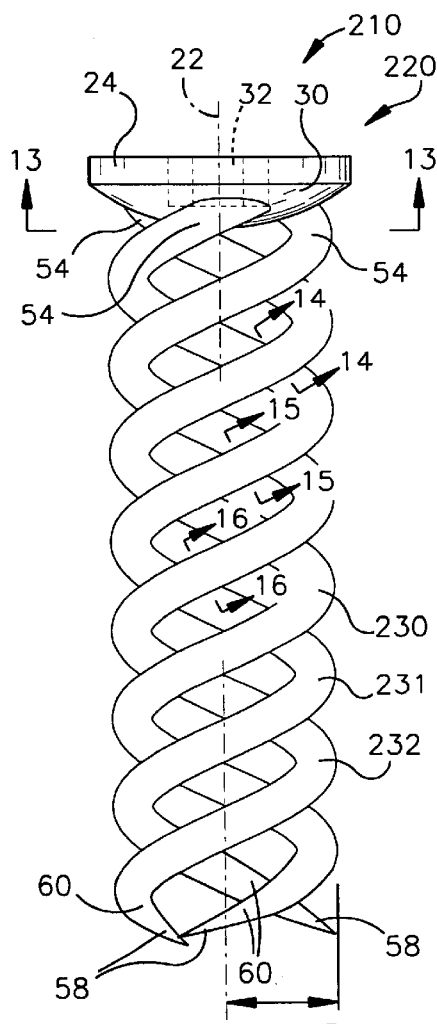
FIG. 12 is a schematic view illustrating an apparatus for attaching fractured sections of bone in accordance with a third embodiment of the present invention.
Figure 13:
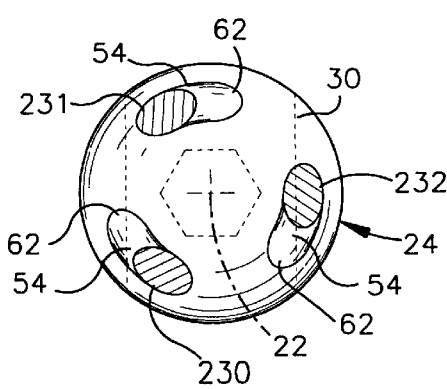
FIG. 13 is a sectional view taken along 13—13 in FIG. 12.

As shown in FIG. 13, the connecting portions 54 at the proximal ends 60 of the helical spikes 230–232 are spaced 120° apart about the axis 22, which balances the bone screw 220 and evenly distributes loads on the helical spikes. As in the first embodiment of FIGS. 1–6, in the third embodiment of FIGS. 12–16, the outer diameter of the connecting portions 54 of the helical spikes 230–232 is greater than or equal to the outer diameter of the intermediate portions 56 and the tip portions 58 of the helical spikes.

Each of the three helical spikes 230–232 extends in a helical pattern about the axis 22 at the same, constant radius R1 (FIG. 12). It is contemplated, however, that one or more of the helical spikes 230–232 could extend about the axis 22 at different radiuses. Further, it is contemplated that the radius of one or more helical spikes 230–232 could increase or decrease as the helical spikes extend away from the platform 24.

As shown in FIG. 12, the three helical spikes 230–232 have the same axial length and also have the same cross-sectional shape. It is contemplated, however, that one or more of the helical spikes 230–232 could have e different axial lengths. Further, it is contemplated that one or more of the helical spikes 230–232 could have a different cross-sectional shape, such as an oval shape. It also contemplated that the one or more of the helical spikes 230–232 could have different outer diameters (i.e., one spike being thicker or thinner than the other spike(s)). Finally, it is contemplated that the helical spikes 230–232 should have the same pitch, and that the pitch of the helical spikes would be selected based on the specific surgical application and quality of the bone in which the bone screw 20 is to be implanted.

It is contemplated that the modified configuration of the helical spikes 50' and 52' illustrated in the second embodiment of FIGS. 8–11 could also be applied to the third embodiment of FIGS. 12–16. Specifically, the connecting portions 54 and/or the tip portions 58 of the helical spikes 230–232 could have a solid cross-section, while the intermediate portions 56 have a tubular cross-section. Such modified configurations of the bone screw 220 provide e additional means for matching the modulus of elasticity of the bone and allow the surgeon to select a particular con figuration based on the specific signal application and quality of the bone in which the bone screw is to be implanted.

The tip portion 58 of each of the helical spikes 230–232 illustrated in FIG. 12 has an elongated conical shape for penetrating into bone as the platform 24 of the bone screw 220 is rotated in the clockwise direction. It should be understood that the tip portions 58 of the helical spikes 230–232 of the bone screw 220 could alternatively be configured like the tip portions illustrated in FIG. 7.

Although the outer surfaces of the helical spikes 230–232 are shown as being smooth in FIGS. 12–16, it is contemplated that the outer surfaces may instead be porous, pitted, or have a biocompatible coating to assist with fixation of the bone screw 220 to the two sections of a fractured bone.

It is further contemplated that the tip portions 58 of the helical spikes 230–232 could be covered with tip protectors (not shown) to prevent accidental sticks to surgical staff and accidental damage to tissue surrounding the fractured bone. Such tip protectors could be made of a bio-absorbable material, such as polylactic acid or a non-bioabsorbable material, such as medical grade silicon. The tip protectors would be manually removed or pushed off during implantation of the bone screw 220.

The bone screw 220 according to the third embodiment of FIGS. 12–16 is implanted in fractured sections of bone, such as the femur 12, in the same manner as the bone screw 20 according to the first embodiment. Because the helical spikes 230–232 of the bone screw 220 displace less cancellous bone during implantation than a conventional solid shank bone screw, less torque is required to implant the bone screw in a fractured bone than is required by a conventional bone screw. Further, because the helical spikes displace only a small amount of bone, the helical spikes do not create a core defect that could lead to bone destruction or failure, such as the helical spikes 230–232 pulling out of the bone. When implanted in a fractured bone, the bone screw 220 according to the third embodiment is highly resistant to being pulled out of the bone and to toggling in the bone despite being subjected to substantial forces caused by human body movement and muscle memory. The bone screw 220 thus provides an effective means for compressing the fractured sections of bone together to prevent relative rotation of the fractured sections and permit healing of the fracture without causing further damage to the fractured sections.

FIGS. 17 and 18 illustrate an apparatus 310 for attaching fractured sections of bone constructed in accordance with a fourth embodiment of the present invention. In the fourth embodiment of FIGS. 17 and 18, reference numbers that are the same as those used in the first embodiment of FIGS. 1–6 designate parts that are the same as parts in the first embodiment.

According to the fourth embodiment, the apparatus 310 comprises a bone screw 320 made at least partially from a shape memory alloy that is biocompatible. As is known in the art, shape memory alloys have the ability to return to a predetermined shape when heated. When a shape memory alloy is cold, or below its transition temperature range (TTR), the material has a low yield strength and can be deformed into a new shape, which it will retain until heated. However, when a shape memory alloy is heated above its TTR, the material undergoes a change in crystal structure (from a martensite structure to an austensite structure), which causes the material to return to its original, or "memorized" shape. A memorized shape is imprinted into a shape memory alloy by first holding the material in the desired shape at a high temperature, and then continuing to hold the material in the desired shape as it cools through its TTR.

The bone screw 320 of the fourth embodiment includes the platform 24 and the helical spikes 50 and 52 of the first embodiment shown in FIGS. 1–6. According to the fourth embodiment, the helical spikes 50 and 52 are made from a shape memory alloy and the shape that is "memorized" into the material of the helical spikes is illustrated in FIG. 18. The memorized shape of the helical spikes 50 and 52 shown in FIG. 18 is slightly axially shorter than the shape of the helical spikes when the temperature of the helical spikes is below the TTR for the shape memory material.

FIGS. 17 and 18 illustrate the helical spikes 50 and 52 embedded in the distal end of a fibula 312 near the distal tibiofibular joint of the fibula and the tibia 313. The fibula 312 has a fracture 314, and the helical spikes 50 and 52 of the bone screw 320 extend across the fracture to attach a fractured section 318 of the fibula to a main body section 317 of the fibula.

The bone screw 320, which has the same basic construction as the bone screw 20 according to the first embodiment except for being made from a shape memory alloy, is implanted in the fibula 312 in the same manner that the bone screw 20 was implanted. The initial rotation of the bone screw 320 screws the helical spikes 50 and 52 into the cancellous bone of the fractured section 318 of the fibula 312. Continued rotation of the bone screw 320 embeds the helical spikes 50 and 52 deeper into the cancellous bone of the fractured section 318 until the tip portions 58 of the helical spikes project into the fracture 314. With the fractured section 318 held firmly against the main body section 317, the platform 24 is further rotated, causing the tip portions 58 of the helical spikes 50 and 52 to penetrate into the main body section of the fibula 312.

The bone screw 320 is rotated until the second end surface 30 on the platform 24 seats against an outer surface 319 on the fractured section 318 as shown in FIG. 17. As may be seen in FIG. 17, even with the second end surface 30 seated against the outer surface 319, there may still be a small gap 322 between the fractured section 318 and the main body section 317. The shape memory effect of the shape memory alloy used for the helical spikes 50 and 52 of the bone screw 320 closes the gap 322 as illustrated in FIG. 18.

As the helical spikes 50 and 52 are screwed into fractured section 318 of the fibula 312, heat is applied to the bone screw 320 until the temperature of the bone screw exceeds the TTR for the shape memory material. Simple body temperature may be sufficient to raise the temperature of the bone screw 320 above its TTR. If additional heat is needed, heat may be applied in several ways, such as passing electric current through a wire connected with the bone screw 320, transmitting radio waves that inductively heat the bone screw, or applying a hot saline pack to the bone screw and adjacent area.

By the time the second end surface 30 on the platform 24 seats against the outer surface 319 on the fractured section 318, the helical spikes 50 and 52 are fully hardened and have nearly completed their shift into their memorized, and axially shorter, shape. As the helical spikes 50 and 52 complete their retraction into the axially shorter shape, this small retraction functions to close the gap 322 between the fractured section 318 and the main body section 317 of the fibula 312. With the fractured section 318 and the main body section 317 attached to each other by the bone screw 320, the fracture 314 in the fibula 312 can heal over time.

As previously discussed with regard to the first embodiment, because the helical spikes 50 and 52 of the bone screw 320 displace less bone in the sections 317 and 318 of the fibula 312 during implantation than a conventional solid shank bone screw, less torque is required to implant the bone screw than is required by a conventional bone screw. Further, the helical spikes do not create a core defect that could lead to bone deformation or failure, such as the helical spikes pulling out of the bone. Also, when implanted, the bone screw 320 is highly resistant to being pulled axially from the bone and to toggling within the bone. The bone screw 320 thus provides an effective means for compressing the fractured sections of bone together to prevent relative rotation of the fractured sections and permit healing of the fracture without causing further damage to the fractured sections.

Figure 19:
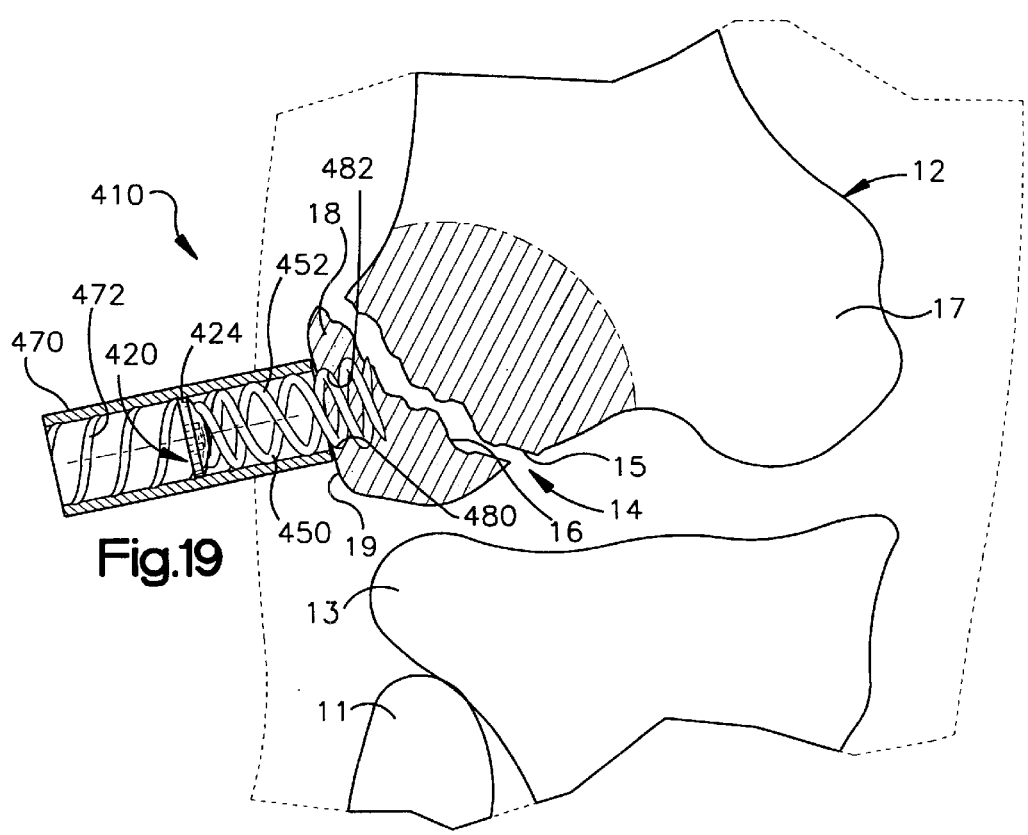
FIG. 19 is a schematic view illustrating an apparatus for attaching fractured sections of bone in accordance with a fifth embodiment of the present invention, the apparatus being shown in a first condition.

FIGS. 19–25 illustrate an apparatus 410 for attaching fractured sections of bone constructed in accordance with a fifth embodiment of the present invention. In the fifth embodiment of FIGS. 19–25, reference numbers that are the same as those used in the first embodiment of FIGS. 1–6 designate parts that are the same as parts in the first embodiment. FIG. 19 illustrates the apparatus 410 partially implanted in the distal end of the femur 12. The fracture 14 in the femur 12, which is defined by the first and second edges 15 and 16, divides the femur into the main body section 17 and the fractured section 18.

According to the fifth embodiment, the apparatus 410 comprises a bone screw 420 made at least partially from a shape memory alloy that is biocompatible. As previously discussed, shape memory alloys have the ability to return to a predetermined shape when heated. When a shape memory alloy is cold, or below its transition temperature range (TTR), the material has a low yield strength and can be deformed into a new shape, which it will retain until heated. However, when a shape memory alloy is heated above its TTR, the material undergoes a change in crystal structure (from a martensite structure to an austensite structure), which causes the material to return to its original, or "memorized" shape. A memorized shape is imprinted into a shape memory alloy by first holding the material in the desired shape at a high temperature, and then continuing to hold the material in the desired shape as it cools through its TTR.

Figure 21:
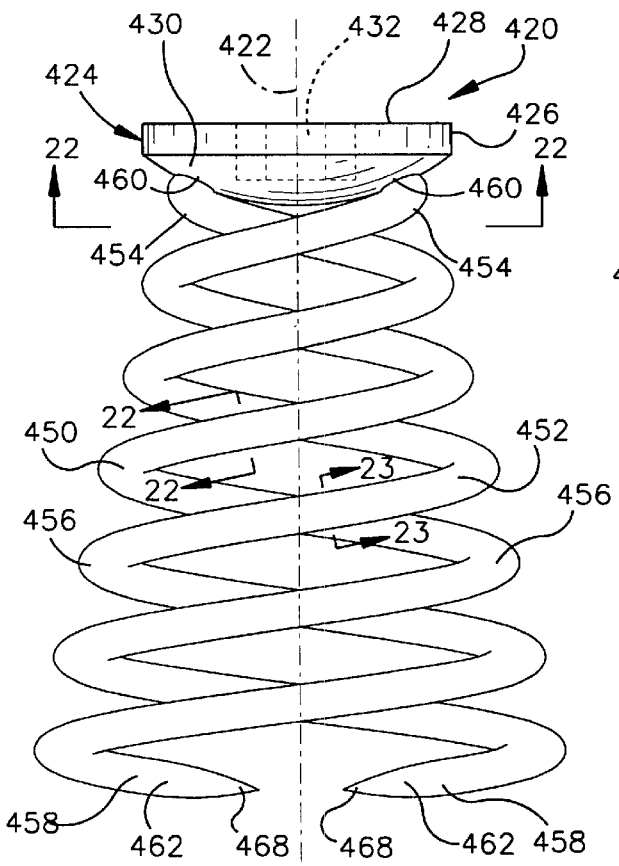
FIG. 21 is a side view of the apparatus of FIG. 20.

As shown in FIG. 21, the bone screw 420 is centered about a longitudinal axis 422. The bone screw 420 includes a platform 424 having a generally cylindrical outer surface 426 extending between oppositely disposed first and second end surfaces 428 and 430 of the platform. The platform 424 includes a hexagonal slot 432 that extends axially from the first end surface 428 toward the second end surface 430 of the platform. The first end surface 428 is planar, while the second end surface 430 has a convex shape that is complimentary to the shape of the outer surface 19 of the fractured section 18 of the femur 12. It should be understood that the second end surface 430 could be any shape that is complimentary to the outer surface 19 of the fractured section 18. The second end surface 430 of the platform 424 may include barbs (not shown) or other suitable structure for fixedly engaging the outer surface 19 of the femur 12. Further, the second end surface 430 of the platform 424 may also be porous, pitted, or have a biocompatible surface coating to assist with fixation of the bone screw 420 to the femur 12.

Figure 23:
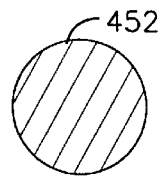
FIG. 23 is a sectional view taken along line 23—23 in FIG. 21.
Figure 23A:
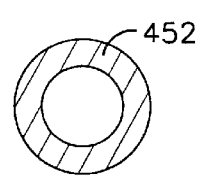
FIG. 23A is a sectional view similar to FIG. 23 illustrating an alternate configuration.
Figure 24:
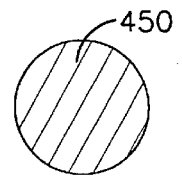
FIG. 24 is a sectional view taken along 24—24 in FIG. 21.
Figure 24A:
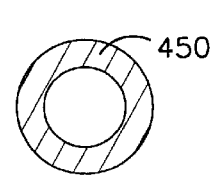
FIG. 24A is a sectional view similar to FIG. 24 illustrating an alternate configuration.

First and second helical spikes 450 and 452 project tangentially from the second end surface 430 of the platform 424. The helical spikes 450 and 452 resemble a pair of intertwined corkscrews, both of which have a conical shape that increases in diameter as the helical spikes extend away from the platform 424. As shown in FIGS. 23 and 24, each of the helical spikes 450 and 452 has a solid cross-section. Alternatively, each of the helical spikes 450 and 452 could have a tubular cross-section, as illustrated in FIGS. 23A and 24A, which provides a means for matching the modulus of elasticity of the bone.

The helical spikes 450 and 452 extend symmetrically in a conical pattern about the axis 422. It is contemplated, however, that the conical shape of the first and second helical spikes 450 and 452 could be different from each other (i.e., one spike being a smaller cone than the other spike). In the illustrated embodiment of FIGS. 19–25, the first and second helical spikes 450 and 452 have the same axial length, and also have the same cross-sectional shape. It is contemplated, however, that the first and second helical spikes 450 and 452 could have different axial lengths. Further, it is contemplated that the helical spikes 450 and 452 could have a different cross-sectional shape, such as an oval shape. It also contemplated that the first and second helical spikes 450 and 452 could have different diameters (i.e., one spike being thicker than the other spike). Finally, it is contemplated that the helical spikes 450 and 452 should have the same pitch, and that the pitch of the helical spikes would be selected based on the specific surgical application and quality of the bone in which the bone screw 420 is to be implanted.

Each of the first and second helical spikes 450 and 452 can be divided into three portions: a connecting portion 454, an intermediate portion 456, and a tip portion 458. The connecting portion 454 of each of the helical spikes 450 and 452 is located at a proximal end 460 that adjoins the end surface 438 of the platform 424. The connecting portion 454 may include barbs (not shown) for resisting pull-out of the helical spikes 450 and 452 from the femur 412. According to one method for manufacturing the bone screw 420, the connecting portion 454 of each of the helical spikes 450 and 452 is fixedly attached to the platform 424 by inserting, in a tangential direction, the proximal ends 460 of the helical spikes into openings (not shown) in the second end surface 430 and welding the connecting portions 454 to the platform. The inserted proximal ends 460 of the helical spikes 450 and 452 help to reduce bending stresses on the helical spikes under tensile or shear loads.

Figure 22:
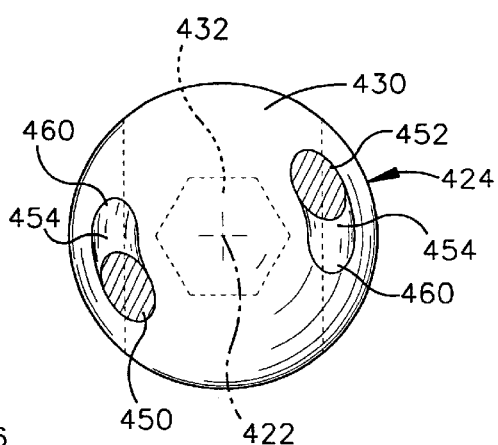
FIG. 22 is a sectional view taken along 22—22 in FIG. 21.

Alternatively, the helical spikes 450 and 452 may be formed integrally with the platform 424, such as by casting the bone screw 420. If the bone screw 420 is cast, it is contemplated that a fillet (not shown) may be added at the junction of the helical spikes 450 and 452 and the platform 424 to strengthen the junction and minimize stress concentrations at the connecting portions 454. The fillet at the junction of the helical spikes 450 and 452 and the platform 424 also helps to reduce bending stresses in the connection portions 454 of the helical spikes under tensile or shear loads. As best seen in FIG. 22, the connecting portions 454 at the proximal ends 460 of the first and second helical spikes 450 and 452 are spaced 180° apart about the axis 422 to balance the bone screw 420 and evenly distribute loads on the helical spikes.

The tip portion 458 of each of the helical spikes 450 and 452 is located at a distal end 462 of the helical spikes. The intermediate portion 456 of each of the helical spikes 450 and 452 extends between the tip portion 458 and the connecting portion 454. The intermediate portion 456 and the tip portion 458 of each of the helical spikes 450 and 452 have a diameter that is less than or equal to the diameter of the connecting portions 454. If the diameter of the intermediate portion 456 and the tip portion 458 is less than the diameter of the connecting portion 454 of each of the helical spikes 450 and 452, the increased thickness of the connecting portions will help to provide the bone screw 420 with increased tensile strength at the junction of the helical spikes and the platform 424.

It is contemplated the modified configuration for the bone screw 20' illustrated in FIGS. 8–11 could be applied to the fifth embodiment of FIGS. 19–25. Accordingly, the connecting portions 454 and/or the tip portions 458 of the helical spikes 450 and 452 could have a solid cross-section, while the intermediate portions 456 have a tubular cross-section. Such modified configurations of the bone screw 420 would provide means for matching the modulus of elasticity of the bone and would allow the surgeon to select a particular configuration based on the specific surgical application and quality of the bone in which the bone screw is to be implanted.

Figure 26:
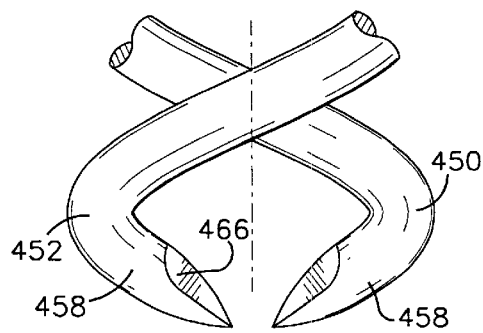
FIG. 26 illustrates an alternate configuration for an end portion of the apparatus of FIG. 20.

Returning now to FIGS. 19–25, the tip portion 458 of each of the helical spikes 450 and 452 has an elongated conical shape with a sharp pointed tip 468 for penetrating into the two sections 17 and 18 of the femur 12 as the platform 424 of the bone screw 420 is rotated in a clockwise direction. FIG. 26 illustrates an alternative, self-tapping configuration' for the tip portions 458 which includes a planar surface 466 for driving into the sections 17 and 18 of the femur 12, in the same manner that a wood chisel turned upside-down drives into wood, as the platform 424 is rotated. It is contemplated that the tip portions 458 could also have a pyramid shape (not shown), similar to the tip of a nail. Although the outer surfaces of the helical spikes 450 and 452 are shown as being relatively smooth in FIGS. 19–25, it is contemplated that the outer surfaces may instead be porous, pitted, or have a biocompatible coating to assist with fixation of the bone screw 420 to the femur 12.

As mentioned previously, the bone screw 420 is made from a shape memory alloy, which allows the bone screw to have more than one shape. FIGS. 25A–25C illustrate the shapes of the bone screw 420 at various stages of the implantation process. The shape that is "memorized" into the material of the bone screw 420 is illustrated in FIGS. 19–21 and 25C. FIG. 25A illustrates the bone screw 420 prior to implantation in the femur 12. As shown in FIG. 25A, prior to implantation, the helical spikes 450 and 452 of the bone screw 420 do not have a conical shape. Rather, prior to implantation, the helical spikes 450 and 452 have a generally cylindrical shape with a uniform maximum diameter D1. Further, prior to implantation, the helical spikes 450 and 452 have an axial length L1. In order for the bone screw 420 to take the shape of FIG. 25A, the temperature of the bone screw must be below its TTR so that the material of the bone screw is soft and ductile.

The bone screw 20 is moved into the shape shown in FIG. 25A with the aid of a tubular sleeve 470. The sleeve 470 is made from a hard metal and includes internal threads 472 (FIG. 25B) for mating with the helical spikes 450 and 452 of the bone screw 420 to aid in drawing the helical spikes into the sleeve upon rotation of the bone screw. With the temperature of the bone screw 420 below its TTR, the bone screw is pulled into the sleeve 470 by rotating the platform 424 in a first direction with a driver (not shown) that fits into the slot 432. As the helical spikes 450 and 452 are drawn into the sleeve 470, the helical spikes are compressed radially inward, causing their axial length to grow to the axial length L1.

FIG. 25B illustrates the bone screw 420 during implantation into the femur 12. As shown in FIG. 25B, the helical spikes 450 and 452 emerge from the sleeve 470 when the platform 424 is rotated in a second direction that is opposite the first direction. As the helical spikes 450 and 452 emerge from the sleeve 470, it is desired that the helical spikes return to the memorized conical shape of FIG. 21. To return the helical spikes 450 and 452 to the conical shape as they emerge from the sleeve 470, heat is applied to the bone screw 420 until the temperature of the bone screw exceeds the TTR for the shape memory material. Simple body temperature may be sufficient to raise the temperature of the bone screw 420 above its TTR. If additional heat is needed, heat may be applied in many ways, such as passing electric current through a wire connected with the bone screw 420 or the sleeve 470, transmitting radio waves that inductively heat the bone screw, or applying a hot saline pack to the sleeve.

With the helical spikes 450 and 452 expanding radially, but contracting axially, as they emerge from the sleeve 470, the helical spikes are implanted in the fractured section 18 of the femur 12 in the conical shape as illustrated in FIG.

25B. FIG. 25C shows the fully implanted bone screw 420 attaching the fractured section 18 to the main body section 17. In FIG. 25C, the helical spikes 450 and 452 have a maximum diameter D2 that is larger than the maximum diameter D1 of the helical spikes prior to implantation. Further, in the implanted condition, the helical spikes 450 and 452 have an axial length L2 that is smaller than the axial length of the helical spikes prior to implantation.

It is contemplated that the shapes of the helical spikes 450 and 452 illustrated in FIGS. 25A–25C could be achieved even if only certain portions of the helical spikes were made from a shape memory alloy. For example, it is contemplated that the tip portions 458 and the intermediate portions 456 of the helical spikes 450 and 452 could be made from a shape memory alloy, while the connecting portions 454 are made from another biocompatible metal. Further, it should be understood that if a shape memory material is not used at all in the helical spikes 450 and 452 and a material such as spring steel is used instead, the helical spikes would still be able to be compressed into the shape of FIG. 25A, and expand into the shapes shown in FIGS. 25B and 25C upon implantation.

Turning now to a more detailed discussion of the procedure for implanting the bone screw 420 to attach the fractured section 18 to the main body section 17, a tool (not shown) is used to punch two holes (not shown) in the fractured section. The holes are punched in locations that correspond to the spacing of the tip portions 458 of the helical spikes 450 and 452 on the bone screw 420 in the shape of FIG. 25A. It should be noted that one or both of the configurations of the tip portions 458 illustrated in FIGS. 19–26 may be able to punch through the cortical bone of the fractured section 18 upon rotation of the bone screw 420, thus eliminating the need for the aforementioned tool to punch holes in the fractured section. The tip portions 458 are then placed in the holes in the fractured section 18 of the femur 12 and a rotatable driver (not shown) is inserted into the slot 432 in the platform 424. The helical spikes 450 and 452 are then heated, as discussed above, to a temperature above the TTR for the shape memory material. The driver is then rotated, causing the bone screw 420 to rotate as well.

Rotation of the bone screw 420 screws the helical spikes 450 and 452 into the cancellous bone of the fractured section 18 of the femur 12. The tangentially-oriented connection between the connecting portions 454 of the helical spikes 450 and 452 and the platform 424, as well as the constraining function of the sleeve 470, minimizes bending loads on the connecting portions during rotation of the bone screw 420. Further, the tangentially-oriented connection ensures that the force vector resulting from torque and axial force applied by the driver to the platform 424 is transmitted along the helical centerline (not shown) of each of the helical spikes 450 and 452.

As the bone screw 420 is rotated, the tip portion 458 of the first helical spike 450 penetrates the cancellous bone and cuts a first conical tunnel 480 (FIG. 19) through the fractured section 18 of the femur 12. Simultaneously, the tip portion 458 of the second helical spike 452 penetrates the cancellous bone of the fractured section 18 and cuts a second conical tunnel 482. The first and second conical tunnels 480 and 482 in the fractured section 18 are shaped like the conical configuration of the helical spikes 450 and 452, respectively, as shown in FIG. 25B. Continued rotation of the bone screw 420 embeds the helical spikes 450 and 452 deeper into the cancellous bone of the fractured section 18 until the tip portions 458 of the helical spikes project through the second edge 16 on the fractured section. With the second edge 16 on the fractured section 18 held firmly against the first edge 15 on the main body section 17, the platform 424 is further rotated, causing the tip portions 458 of the helical spikes 450 and 452 to penetrate through the first edge and into the main body section of the femur 12.

Figure 20:
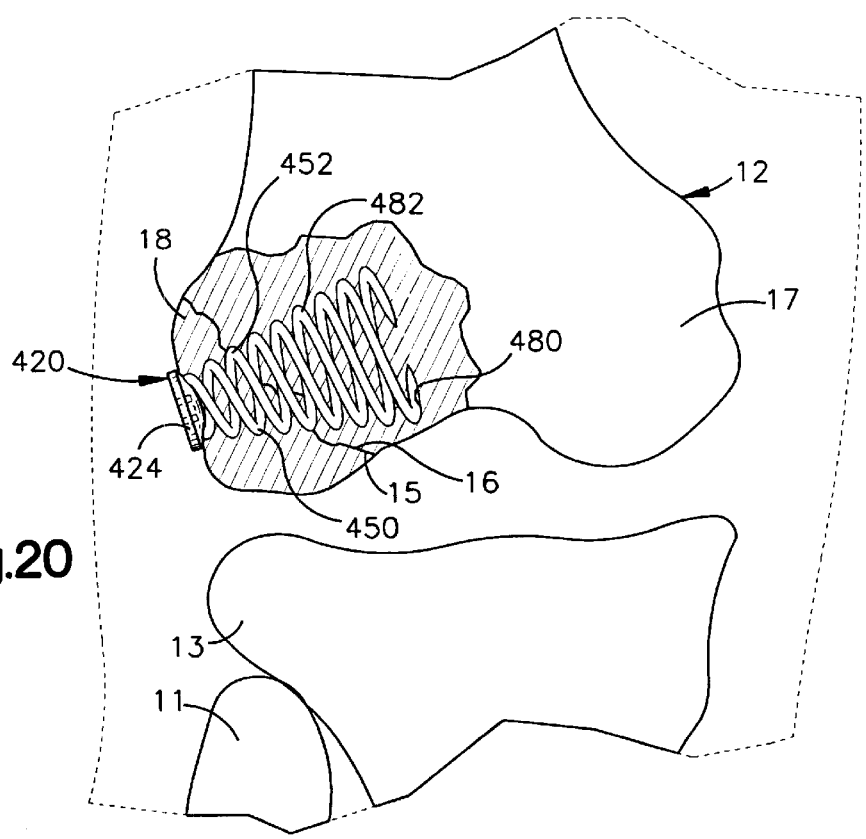
FIG. 20 is a view similar to FIG. 19 illustrating the apparatus in a second condition.

As the bone screw 420 is rotated further, the first and second helical spikes 450 and 452 cut into the main body section 17 and extend the first and second conical tunnels 480 and 482, respectively, into the main body section (see FIG. 20). The first and second conical tunnels 480 and 482 in the main body section 17 are shaped like the conical configuration of the helical spikes 450 and 452, respectively, as shown in FIG. 25C. The bone screw 420 is rotated until the second end surface 430 on the platform 424 seats tightly against the outer surface 19 of the fractured section 18 as shown in FIG. 20. As the second end surface 430 on the platform 424 seats tightly against the outer surface 19, the first and second edges 15 and 16 are moved into engagement with each other. With the fractured section 18 and the main body section 17 attached to each other by the bone screw 420, the fracture 14 in the femur 12 can heal over time.

Because the helical spikes 450 and 452 of the bone screw 420 displace much less of the cancellous bone of the femur 12 during implantation than a conventional solid shank bone screw, much less torque is required to implant the bone screw in the femur than is required by a conventional bone screw. Further, because the helical spikes 450 and 452 displace only a small amount of bone, the helical spikes do not create a core defect that could lead to bone deformation or failure, such as the helical spikes pulling out of the femur 12. Advantageously, the conical shape of the helical spikes 450 and 452 increases the amount of surface area engaged by the bone screw 420, spreads any load on the bone screw out over different areas of the sections 17 and 18 of the femur 12, and provides fixation over a larger volume of bone. The aforementioned advantages of the conical shape of the helical spikes 450 and 452 are especially helpful when implanting the bone screw 420 in osteoporotic bone.

When the helical spikes 450 and 452 are embedded in the sections 17 and 18 of the femur 12, the conical shape of the two helical spikes provides the bone screw 420 with a high resistance to pull-out forces and a high resistance to toggling in the femur. Finally, the use of a shape memory alloy for the helical spikes 450 and 452 allows the bone screw 420 to have a smaller diameter prior to implantation, which permits minimally invasive or endoscopic surgery through a cannula, and a wider diameter when implanted, which improves fixation of the fractured section 18 to the main body section 17 of the femur 12. The bone screw 420 thus provides an effective means for compressing the fractured sections 17 and 18 of the femur 12 together to prevent relative rotation of the fractured sections and permit healing of the fracture without causing further damage to the fractured sections.

FIGS. 27–31 illustrate an apparatus 510 for attaching fractured sections of bone in accordance with a sixth embodiment of the present invention. In the sixth embodiment of FIGS. 27–31, reference numbers that are the same as those used in the fifth embodiment of FIGS. 19–25 designate parts that are the same as parts in the fifth embodiment.

Figures 29, 29A:
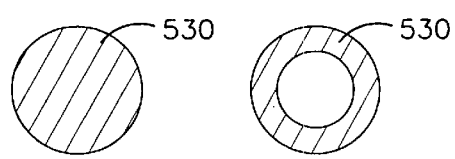
FIG. 29 is a sectional view taken along 29—29 in FIG. 27.
FIG. 29A is a sectional view similar to FIG. 29 illustrating an alternate configuration.
Figures 30, 30A:
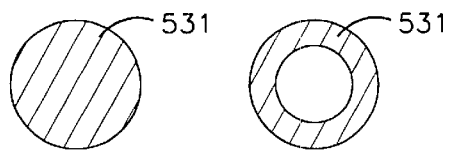
FIG. 30 is a sectional view taken along 30—30 in FIG. 27.
FIG. 30A is a sectional view similar to FIG. 30 illustrating an alternate configuration.
Figures 31, 31A:
FIG. 31 is a sectional view taken along 31—31 in FIG. 27.
FIG. 31A is a sectional view similar to FIG. 31 illustrating an alternate configuration.

According to the sixth embodiment, the apparatus 210 comprises a bone screw 520 having three helical spikes 530, 531, and 532 projecting tangentially from the second end surface 430 of the platform 424. The spikes 530–532 extend around the axis 422 and have a conical shape that increases in diameter as the helical spikes extend away from the platform. As shown in FIGS. 29–31, each of the helical spikes 530–532 has a solid cross-section. Alternatively, each of the helical spikes 530–532 could have a tubular cross-section as shown in FIGS. 29A–31A, which provides a means for matching the modulus of elasticity of the bone.

Figure 27:
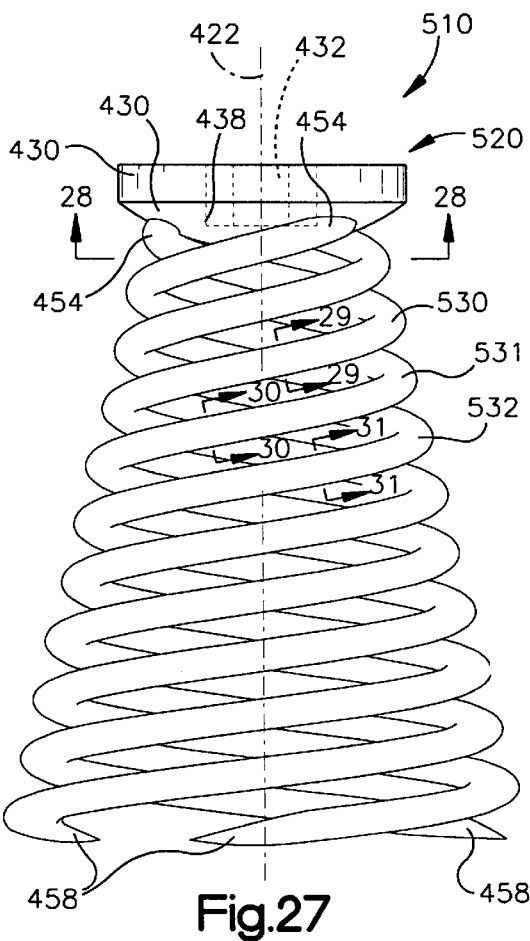
FIG. 27 is a side view illustrating an apparatus for attaching fractured sections of bone in accordance with a sixth embodiment of the present invention.
Figure 28:
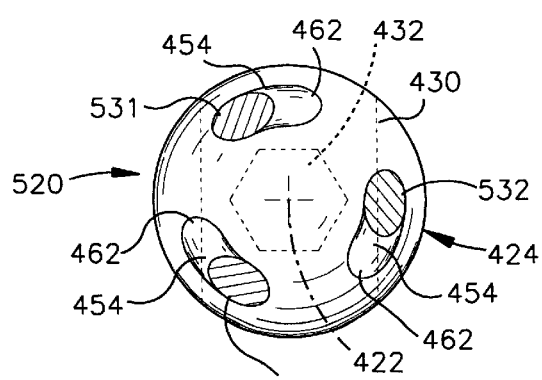
FIG. 28 is a sectional view taken along line 28—28 in FIG. 27.

As shown in FIG. 28, the connecting portions 454 at the proximal ends 460 of the helical spikes 530–532 are spaced 120° apart about the axis 422, which balances the bone screw 520 and evenly distributes loads on the helical spikes. As in the fifth embodiment of FIGS. 19–25, in the sixth embodiment of FIGS. 27–31, the outer diameter of the connecting portions 454 of the helical spikes 530–532 is greater than or equal to the outer diameter of the intermediate portions 456 and the tip portions 458 of the helical spikes.

The three helical spikes 530–532 extend symmetrically in a conical pattern about the axis 422. It is contemplated, however, that the conical shape of one or more of the helical spikes 530–532 could be different from the other(s) (i.e., one spike being a smaller cone than the others). As shown in FIG. 27, the three helical spikes 530–532 have the same axial length and also have the same cross-sectional shape. It is contemplated, however, that one or more of the helical spikes 530–532 could have different axial lengths. Further, it is contemplated that one or more of the helical spikes 530–532 could have a different cross-sectional shape, such as an oval shape. It also contemplated that the one or more of the helical spikes 530–532 could have different diameters (i.e., one spike being thicker or thinner than the other spike(s)). Finally, it is contemplated that the helical spikes 530–532 should have the same pitch, and that the pitch of the helical spikes would be selected based on the specific surgical application and quality of the bone in which the bone screw 520 is to be implanted.

It is contemplated that the modified configuration of the helical spikes 50' and 52' according to the second embodiment illustrated in FIGS. 8–11 could also be applied to the sixth embodiment of FIGS. 27–31. Specifically, the connecting portions 454 and/or the tip portions 458 of the helical spikes 530–532 could have a solid cross-section, while the intermediate portions 456 have a tubular cross-section. Such modified configurations of the bone screw 520 provide additional means for matching the modulus of elasticity of the bone.

The tip portion 458 of each of the helical spikes 530–532 illustrated in FIG. 27 has an elongated conical shape for penetrating into the sections 17 and 18 of the femur 12 as the platform 424 of the bone screw 520 is rotated in the clockwise direction. It should be understood that the tip portions 458 of the helical spikes 530–532 of the bone screw 520 could alternatively be configured like the tip portions illustrated in FIG. 26. Further, although the outer surfaces of the helical spikes 530–532 are shown as being smooth in FIGS. 27–31, it is contemplated that the outer surfaces may instead be porous, pitted, or have a biocompatible coating to assist with fixation of the bone screw 520 to the femur.

The helical spikes 530–532 of the bone screw 520 according to the sixth embodiment of FIGS. 27–31 are also made of a shape memory alloy and are implanted in the sections 17 and 18 of the femur 12 in the same manner as the bone screw 420 according to the fifth embodiment. The shapes of the bone screw 520 at various stages of the implantation process are similar to that which is illustrated in FIGS. 25A–25C for the bone screw 420 of the fifth embodiment. Hence, the shape that is "memorized" into the material of the bone screw 520 is illustrated in FIG. 27. Further, as shown in FIG. 25A, prior to implantation, the helical spikes 530–532 of the bone screw 520 do not have a conical shape, but instead have a generally cylindrical shape with a first maximum diameter and a first axial length. In order for the bone screw 520 to take the shape of FIG. 25A, the temperature of the bone screw must be below its TTR so that the material of the bone screw is soft and ductile. As in the fifth embodiment of FIGS. 19–25, the bone screw 520 is also moved into the shape of FIG. 25A with the aid of the tubular sleeve 470.

To return the helical spikes 530–532 to the conical shape of FIGS. 25B and 25C as they emerge from the sleeve 470, heat is applied to the bone screw 520 until the temperature of the bone screw exceeds the TTR for the shape memory material. With the helical spikes 530–532 expanding radially and contracting axially as they emerge from the sleeve 470, the helical spikes are implanted in the fractured section 18 of the femur 12 in the conical shape illustrated in FIG. 25C for the fifth embodiment. In FIG. 25C, the helical spikes 530–532 have a second maximum diameter that is larger than the first maximum diameter of the helical spikes prior to implantation, and have a second axial length that is smaller than the first axial length of the helical spikes prior to implantation.

It is contemplated that the shapes of the helical spikes 530-532 illustrated in FIGS. 25A–25C could be achieved even if only certain portions of the helical spikes were made from a shape memory alloy. For example, it is contemplated that the tip portions 458 and the intermediate portions 456 of the helical spikes 530–532 could be made from a shape memory alloy, while the connecting portions 454 are made from another biocompatible metal. Further, if a shape memory material is not used at all in the helical spikes 530–532 and a material such as spring steel is used instead, the helical spikes would still be able to be compressed into the shape of FIG. 25A, and expand into the shapes shown in FIGS. 25B and 25C upon implantation.

As mentioned previously, the bone screw 520 is used to attach the sections 17 and 18 of the femur 12 in the same manner as the bone screw 420 according to the fifth embodiment. With the fractured section 18 and the main body section 17 of the femur 12 attached to each other by the bone screw 520, the fracture 14 in the femur 12 can heal over time. Because the helical spikes 530–532 of the bone screw 520 displace less cancellous bone during implantation than a conventional solid shank bone screw, less torque is required to implant the bone screw in a bone than is required by a conventional bone screw. Further, because the helical spikes 530–532 displace only a small amount of bone, the helical spikes do not create a core defect that could lead to bone deformation or failure, such as the helical spikes pulling out of the bone.

Advantageously, the conical shape of the helical spikes 530–532 increases the amount of surface area engaged by the bone screw 520, spreads any load on the bone screw out over different areas of the sections 17 and 18 of the femur 12, and provides fixation over a larger volume of bone. These advantages of the conical shape of the helical spikes 530–532 are especially helpful when implanting the bone screw 520 in osteoporotic bone.

When implanted in the sections 17 and 18 of the femur 12, the conical shape of the helical spikes 530–532 according to the sixth embodiment make the bone screw 520 highly resistant to being pulled out of the femur and to toggling in the femur despite being subjected to substantial forces caused by human body movement and muscle memory. Finally, the use of a shape memory alloy for the helical spikes 530–532 allows the bone screw 520 to have a smaller diameter prior to implantation, which permits minimally invasive or endoscopic surgery through a cannula, and a wider diameter when implanted, which improves fixation in the femur. The bone screw 520 thus provides an effective means for compressing the fractured sections of bone together to prevent relative rotation of the fractured sections and permit healing of the fracture without causing further damage to the fractured sections.

Figure 32:
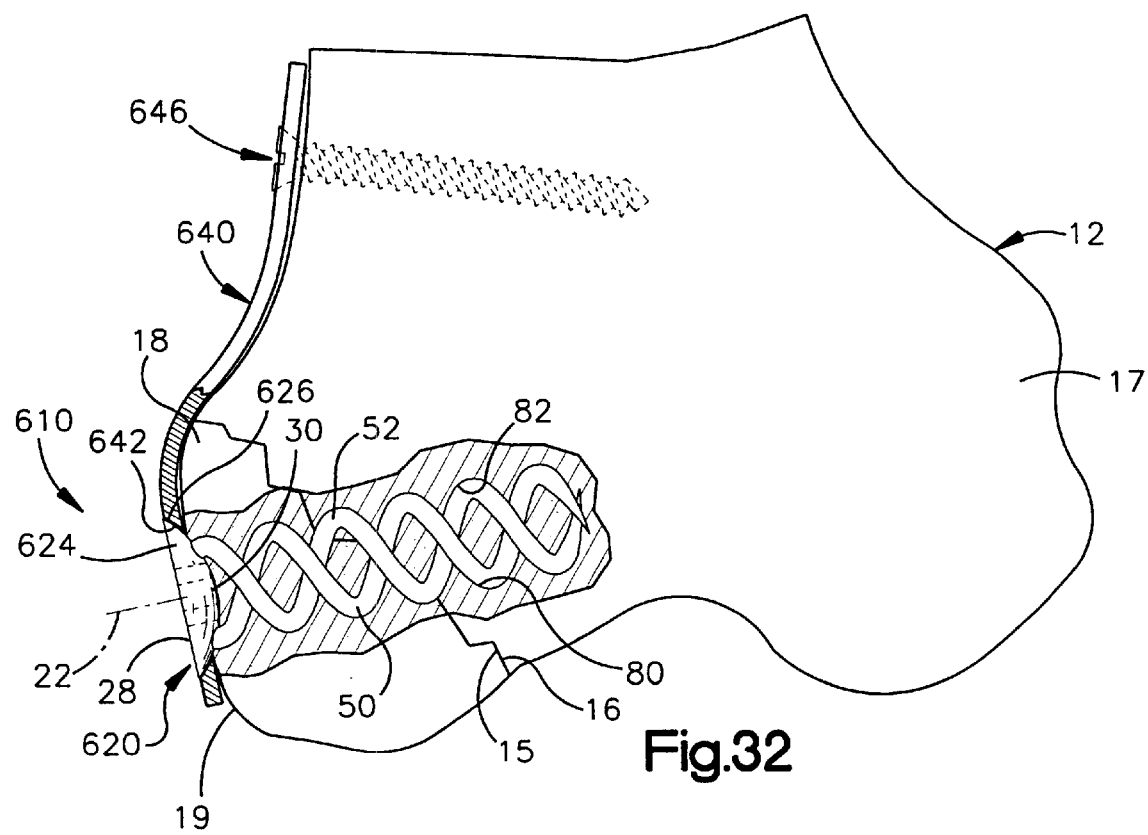
FIG. 32 is a schematic view illustrating an apparatus for attaching fractured sections of bone in accordance with a seventh embodiment of the present invention.

FIG. 32 illustrates an apparatus 610 for attaching fractured sections of bone in accordance with a seventh embodiment of the present invention. In the seventh embodiment of FIG. 32, reference numbers that are the same as those used in the first embodiment of FIGS. 1–6 designate parts that are the same as parts in the first embodiment.

According to the seventh embodiment, the apparatus 610 comprises a bone screw 620. The bone screw 620 is nearly identical to the bone screw 20 according to the first embodiment, including the helical spikes 50 and 52. However, the difference between the bone screw 20 of the first embodiment and the bone screw 620 according to the seventh embodiment is that the bone screw 620 has a platform 624 that is different than the platform 24. The platform 624 does not have a cylindrical outer surface, such the cylindrical outer surface 26 of the platform 24.

Rather, the platform 624 includes a tapered outer surface 626 which extends between the first end surface 28 and the second end surface 30.

The bone screw 620 according to the seventh embodiment is particularly useful when a plate, such as the plate 640, is also used to help secure the fractured section 18 of a bone, such the femur 12, to the main body section 17. The plate 640 has been shaped to match the profile of the distal end of the femur 12. The plate 640 includes a first opening (not numbered) with a tapered inner surface 642 for receiving the tapered outer surface 626 of the platform 624 of the bone screw 620. The plate 640 also includes one or more additional openings (not numbered) for receiving conventional bone screws, such as the bone screw 646 shown in FIG. 32.

The bone screw 620 according to the seventh embodiment of FIG. 32 is implanted in the fractured section 18 and the main body section 17 of the femur 12 in the same manner as the bone screw 20 according to the first embodiment. When implanted, the bone screw 620 clamps down on the plate 640, which is present to help further stabilize the fracture 14 in the femur 12. Because the helical spikes 50 and 52 of the bone screw 620 displace less cancellous bone during implantation than a conventional solid shank bone screw, less torque is required to implant the bone screw in a fractured bone than is required by a conventional bone screw. Further, because the helical spikes 50 and 52 displace only a small amount of bone, the helical spikes do not create a core defect that could lead to bone destruction or failure, such as the helical spikes 50 and 52 pulling out of the bone. Finally, the bone screw 620 according to the seventh embodiment, when implanted in a fractured bone, is highly resistant to being pulled out of the bone and to toggling in the bone despite being subjected to substantial forces caused by human body movement and muscle memory. The bone screw 620 thus provides an effective means for compressing the fractured sections of bone together to prevent relative rotation of the fractured sections and permit healing of the fracture without causing further damage to the fractured sections.

Figure 33A:
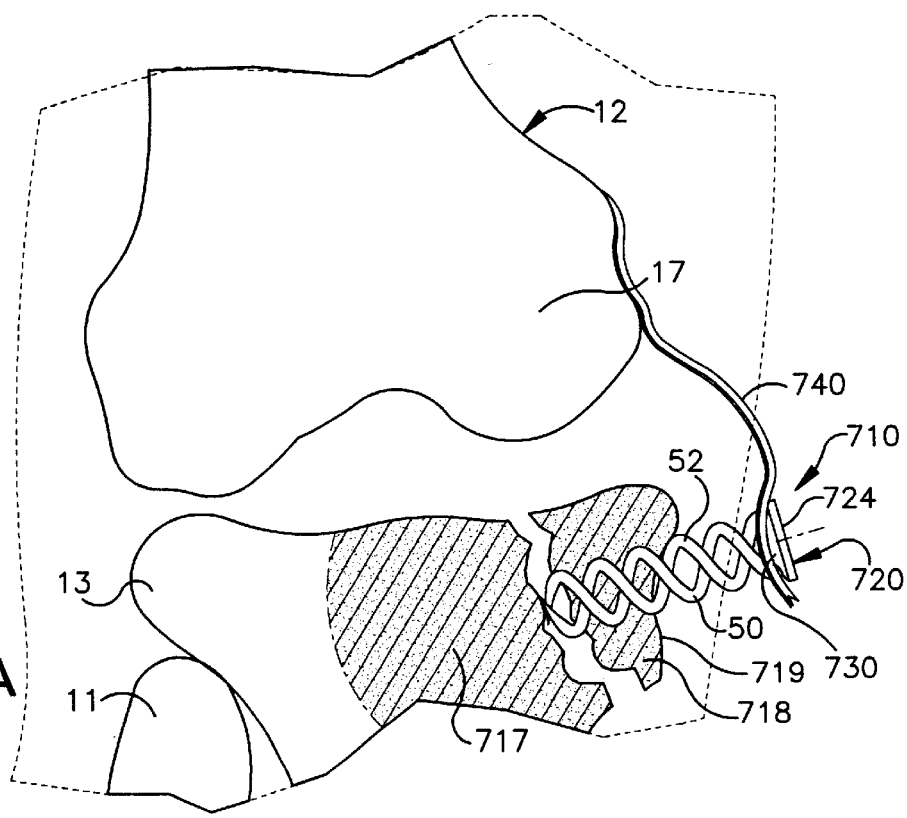
FIG. 33A is a schematic view illustrating an apparatus for attaching fractured sections of bone in accordance with an eighth embodiment of the present invention, the apparatus being shown in a first condition.
Figure 33B:
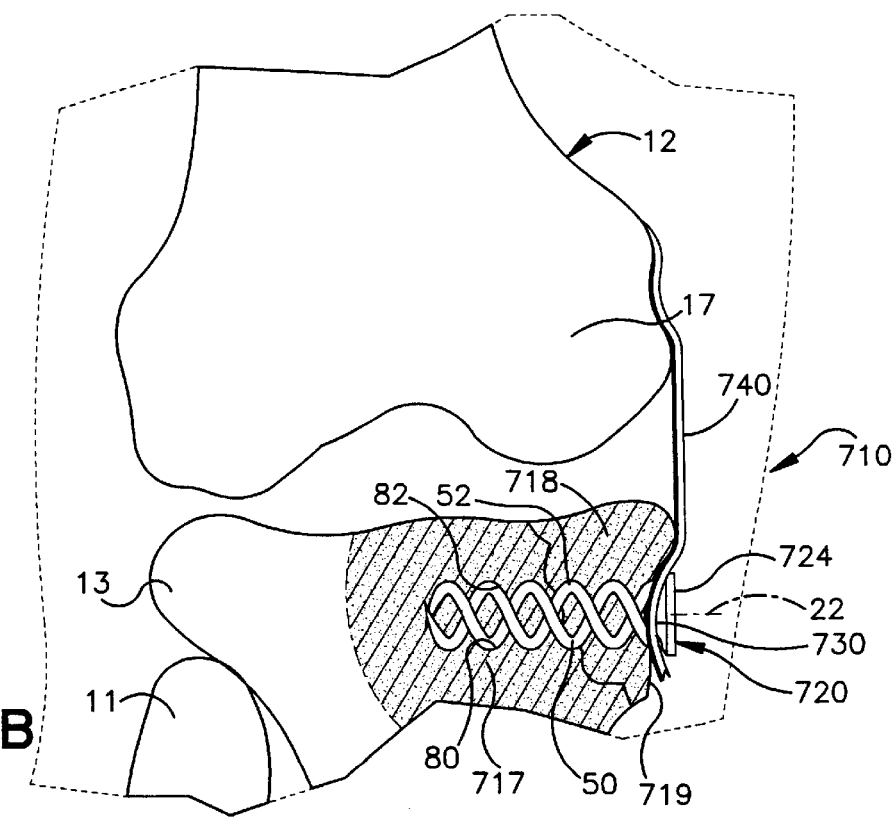
FIG. 33B is a view similar to FIG. 33A illustrating the apparatus in a second condition.

FIGS. 33A and 33B illustrate an apparatus 710 for attaching fractured sections of bone in accordance with an eighth embodiment of the present invention. In the eighth embodiment of FIGS. 33A and 33B, reference numbers that are the same as those used in the first embodiment of FIGS. 1–6 designate parts that are the same as parts in the first embodiment.

According to the eighth embodiment, the apparatus 710 comprises a bone screw 720. The bone screw 720 is nearly identical to the bone screw 20 according to the first embodiment, including the helical spikes 50 and 52. However, the bone screw 720 according to the eighth embodiment has a platform 724 that is slightly different from the platform 24 of the bone screw 20 according to the first embodiment. The platform 724 is wider than the platform 20 and has a second end surface 730 that can include a planar surface portion (not shown). The second end surface 730 faces toward an outer surface 719 of a fractured section 718 of the tibia 13.

The bone screw 720 according to the eighth embodiment is particularly useful when, in addition to securing the fractured section 718 to a main body section 717 of the tibia 13, the bone screw functions as a tissue anchor to secure soft tissue, such as a tendon or ligament 740 shown schematically in FIGS. 33A and 33B, to the tibia 13.

The bone screw 720 according to the eighth embodiment of FIGS. 33A and 3B is implanted in the fractured section 718 and the main body section 717 of the tibia 13 in the same manner as the bone screw 20 according to the first embodiment is implanted in the femur 12. When implanted, the bone screw 720 compresses the sections 717 and 717 of the tibia 13 together and also clamps down on the ligament 740 to attach, or anchor, the ligament to the tibia. The attachment of the ligament 740 to the proximal end of the tibia 13 reduces the knee joint from the open position shown in FIG. 33A to its proper anatomical alignment shown in FIG. 33B.

Because the helical spikes 50 and 52 of the bone screw 720 displace less cancellous bone during implantation than a conventional solid shank bone screw, less torque is required to implant the bone screw in a fractured bone than is required by a conventional bone screw. Further, because the helical spikes 50 and 52 displace only a small amount of bone, the helical spikes do not create a core defect that could lead to bone destruction or failure, such as the helical spikes 50 and 52 pulling out of the bone. When implanted in a fractured bone, the bone screw 720 is highly resistant to being pulled out of the bone and to toggling in the bone despite being subjected to substantial forces caused by human body movement and muscle memory. The bone screw 720 thus provides an effective means for compressing the fractured sections of bone together to prevent relative rotation of the fractured sections and permit healing of the fracture without causing further damage to the fractured sections.

FIGS. 34 and 35 illustrate an apparatus 810 for attaching fractured sections of bone in accordance with a ninth embodiment of the present invention. In the ninth embodiment of FIGS. 34 and 35, reference numbers that are the same as those used in the first embodiment of FIGS. 1–6 designate parts that are the same as parts in the first embodiment.

The ninth embodiment of the present invention is directed to a hip fixation device. According to the ninth embodiment, the apparatus 810 includes a bone screw 820 implanted in a neck section 818 at the proximal end of a femur 812. The neck section 818 and the associated head 821 of the femur 812 are separated from a main body section 817 of the femur by a fracture 814. The fracture 814 is defined by opposing first and second edges 815 and 816. The neck section 818 includes the first edge 815. The main body section 817 includes the second edge 816 and an outer surface 819.

The bone screw 820 made from a biocompatible material, such as titanium or stainless steel. It is contemplated that the biocompatible material used for the bone screw 820 could be polymeric or composite (i.e., carbon fiber or other biologic composite) in nature.

The bone screw 820 is centered about a longitudinal axis 822 (FIG. 34). The bone screw 820 includes a platform 824 comprising a cylindrical body portion 826 extending between oppositely disposed first and second end surfaces 828 and 830 of the platform. The body portion 826 includes a threaded outer surface portion 829 adjacent the first end surface 828.

The first end surface 828 of the platform 824 is planar and includes a hexagonal slot 832 that extends axially from the first end surface toward the second end surface 830 of the platform. The hexagonal slot 832 is designed to receive a driver (not shown) for rotating the bone screw 820.

The first and second helical spikes 50 and 52, which were described in detail in the first embodiment of FIGS. 1–6, project tangentially from the second end surface 830 of the platform 824. The helical spikes 50 and 52 resemble a pair of intertwined corkscrews.

The apparatus 810 according to the ninth embodiment further includes a plate member 840 and a nut 890. The plate member 840 includes a plate section 842 and a sleeve section 844 located at a first end 845 of the plate section. The plate section 842 is designed to abut the outer surface 819 of the main body portion 817 of the femur 812. The sleeve section 844 includes a passage 880 centered on the axis 822. The passage 880 is adapted to receive the body portion 826 of the platform 824.

To use the apparatus 810 to attach the fractured neck section 818 to the main body section 817 of the femur 812, the sleeve section 844 of the plate member 840 is implanted in the proximal end of the femur 812 as shown in FIGS. 34 and 35 and known in the art. A second end 847 of the plate section 842 is attached to the main body portion 817 of the femur 812 by conventional bone screws 848.

A cylindrical bore 850 is then drilled into the neck section 818 along the axis 822. The helical spikes 50 and 52 and the body portion 826 of the platform 824 are inserted into the passage 880 in the sleeve section 844 and are pushed across the fracture 814 and into the bore 850 in the neck section 818. The helical spikes 50 and 52 and the body portion 826 of the platform 824 are pushed into the bore 850 until the helical spikes engage the end 852 of the bore in the head 821 of the femur 812.

A rotatable driver (not shown) is then inserted into the slot 832 in the platform 824 and the driver is rotated, causing the bone screw 820 to rotate as well. Rotation of the bone screw 820 screws the helical spikes 50 and 52 into the cancellous bone of the head 821 of the femur 812. As the bone screw 820 is rotated, the tip portions 58 of the helical spikes 50 and 52 penetrate the cancellous bone of the head 821 and cut corresponding helical tunnels (not numbered) into the head. Continued rotation of the bone screw 820 embeds the helical spikes 50 and 52 deeper into the cancellous bone of the head 821 until the second end surface 830 engages the end 852 of the bore 850.

Next, the main body section 817 of the femur 812 and the neck section 818 are moved from the positions shown in FIG. 34 to the positions shown in FIG. 35 by pressing the main body section and the neck section together. Pressing the main body section 817 and the neck section 818 together slides the body portion 826 of the bone screw 820 farther into the passage 880 in the sleeve section 844. The neck section 818 and the main body portion 817 of the femur 812 are moved toward each other until the first and second edges 815 and 816 of the fracture 814 engage each other, as shown in FIG. 35. In this position, the threaded outer surface portion 829 of the body portion 826 projects out of the passage 880 and the nut 890 is tightened on the threaded outer surface portion to attach the neck section 818 and the main body section 817. With the neck section 818 and the main body section 817 attached to each other by the bone screw 820, the fracture 814 in the femur 812 can heal over time.

Because the helical spikes 50 and 52 of the bone screw 820 displace much less of the cancellous bone in the neck section 818 of the femur 812 during implantation than a conventional solid shank bone screw, much less torque is required to implant the bone screw in the femur than is required by a conventional bone screw. Further, because the helical spikes 50 and 52 displace only a small amount of bone, the helical spikes do not create a core defect that could lead to bone deformation or failure, such as the helical spikes pulling out of the bone. When implanted, the helical spikes 50 and 52 provide the bone screw 820 with a high resistance to pull-out forces. Further, the helical spikes 50 and 52 provide the bone screw 820 with a high resistance to toggling in the bone. The bone screw 820 thus provides an effective means for compressing the fractured sections of bone together to prevent relative rotation of the fractured sections and permit healing of the fracture without causing further damage to the fractured sections.

FIGS. 36 and 37 illustrate an apparatus 910 for attaching fractured sections of bone in accordance with a tenth embodiment of the present invention. In the tenth embodiment of FIGS. 36 and 37, reference numbers that are the same as those used in the ninth embodiment of FIGS. 34 and 35 designate parts that are the same as parts in the ninth embodiment.

The tenth embodiment of the present invention is also directed to a hip fixation device. According to the tenth embodiment, the apparatus 910 includes a bone screw 920 implanted in the neck section 818 and associated head 821 at the proximal end of the femur 812. The bone screw 920 has the first and second conically-shaped helical spikes 450 and 452 which were described in detail with regard to the fifth embodiment of FIGS. 19–25.

The helical spikes 450 and 452 extend symmetrically in a conical pattern about the axis 822. It is contemplated, however, that the conical shape of one or more of the helical spikes 450 and 452 could be different from the other(s) (i.e., one spike being a smaller cone than the others). The helical spikes 450 and 452 have the same axial length and also have the same cross-sectional shape. It is contemplated, however, that one or more of the helical spikes 450 and 452 could have different axial lengths. Further, it is contemplated that one or more of the helical spikes 450 and 452 could have a different cross-sectional shape, such as an oval shape. It also contemplated that the one or more of the helical spikes 450 and 452 could have different diameters (i.e., one spike being thicker or thinner than the other spike(s)). Finally, it is contemplated that the helical spikes 450 and 452 should have the same pitch, and that the pitch of the helical spikes would be selected based on the specific surgical application and quality of the bone in which the bone screw 920 is to be implanted.

The tip portion 458 of each of the helical spikes 450 and 452 illustrated in FIG. 36 has an elongated conical shape for penetrating into the head 821 of the femur 812 as the platform 824 of the bone screw 920 is rotated in the clockwise direction. It should be understood that the tip portions 458 of the helical spikes 450 and 452 of the bone screw 920 could alternatively be configured like the tip portions illustrated in FIG. 26. Further, although the outer surfaces of the helical spikes 450 and 452 are shown as being smooth in FIGS. 36 and 37, it is contemplated that the outer surfaces may instead be porous, pitted, or have a biocompatible coating to assist with fixation of the bone screw 920 to the femur.

The helical spikes 450 and 452 of the bone screw 920 according to the tenth embodiment of FIGS. 36 and 37 are also made of a shape memory alloy and are implanted in the head 821 of the femur 812 in the same manner as the bone screw 420 according to the fifth embodiment. The shapes of the bone screw 920 at various stages of the implantation process are similar to that which is illustrated in FIGS. 25A–25C for the bone screw 420 of the fifth embodiment. Hence, the shape that is "memorized" into the material of the bone screw 920 is illustrated in FIGS. 36 and 37. Further, prior to implantation, the helical spikes 450 and 452 of the bone screw 920 do not have a conical shape, but instead have a generally cylindrical shape (not shown) with a first maximum diameter and a first axial length. In order for the bone screw 920 to take this cylindrical shape, the temperature of the bone screw must be below its TTR so that the material of the bone screw is soft and ductile. Similar to the fifth embodiment of FIGS. 19–25, the bone screw 920 is moved into the cylindrical shape with the aid of a sleeve. In the tenth embodiment of FIGS. 36 and 37, the sleeve section 844 of the plate member 840 performs this function.

To return the helical spikes 450 and 452 to the conical shape of FIGS. 36 and 37 as they are implanted in the head 821 of the femur 812, heat is applied to the bone screw 920 until the temperature of the bone screw exceeds the TTR for the shape memory material. The helical spikes 450 and 452 thus expand radially and contract axially as they are implanted in the head 821. In the implanted condition of FIGS. 36 and 37, the helical spikes 450 and 452 have a second maximum diameter that is larger than the first maximum diameter of the helical spikes prior to implantation, and have a second axial length that is smaller than the first axial length of the helical spikes prior to implantation.

It is contemplated that the shape changes of the helical spikes 450 and 452 could be achieved even if only certain portions of the helical spikes were made from a shape memory alloy. For example, it is contemplated that the tip portions 458 and the intermediate portions 456 of the helical spikes 450 and 452 could be made from a shape memory alloy, while the connecting portions 454 are made from another biocompatible metal. Further, if a shape memory material is not used at all in the helical spikes 450 and 452 and a material such as spring steel is used instead, the helical spikes would still be able to be compressed into the cylindrical shape, and expand into the conical shape upon implantation.

The apparatus 910, which includes the plate member 840 and the nut 890, is used to attach the head 821 and neck section 818 to the main body section 817 of the femur 812 in the same manner as described with regard to the ninth embodiment of FIGS. 34 and 35. The sleeve section 844 of the plate member 840 is implanted in the proximal end of the femur 812 and the second end 847 of the plate section 842 is attached to the main body portion 817 of the femur 812 by conventional bone screws 848.

The cylindrical bore 850 is then drilled in the neck section 818 along the axis 822. The helical spikes 450 and 452 and the body portion 826 of the platform 824 are inserted into the passage 880 in the sleeve section 844 and are pushed across the fracture 814 and into the bore 850 in the neck section 818. The helical spikes 450 and 452 and the body portion 826 of the platform 824 are pushed into the bore 850 until the helical spikes engage the end 852 of the bore in the head 821.

After heating the helical spikes 450 and 452 above their TTR, a rotatable driver (not shown) is inserted into the slot 832 in the platform 824 and the driver is rotated, causing the bone screw 820 to rotate as well. Rotation of the bone screw 820 screws the helical spikes 450 and 452 into the cancellous bone of the head 821. As the bone screw 820 is rotated, the tip portions 58 of the helical spikes 450 and 452 penetrate the head 821 and cut corresponding helical tunnels (not numbered) through the head of the femur 812. Continued rotation of the bone screw 820 embeds the conically-shaped helical spikes 450 and 452 deeper into the cancellous bone of the head 821 until the second end surface 830 engages the end 852 of the bore 850.

Next, the main body section 817 of the femur 812 and the neck section 818 are moved from the positions shown in FIG. 36 to the positions shown in FIG. 37 by pressing the main body section and the neck section together. Pressing the main body section 817 and the neck 818 together slides the body portion 826 of the bone screw 820 farther into the passage 880 in the sleeve section 844. The neck section 818 and the main body portion 817 of the femur 812 are moved toward each other until the first and second edges 815 and 816 of the fracture 814 engage e each other, as shown in FIG. 37. In this position, the threaded outer surface portion 829 of the body portion 826 projects out of the pass age 880 and the nut 890 is tightened on the threaded outer surface portion to attach the neck section 818 and the main body section 817. Wit h the neck section 818 and the main body section 817 attached to each other by the bone screw 820, the fracture 814 in the femur 812 can heal over time.

Because the helical spikes 450 and 452 of the bone screw 920 displace less cancellous bone during implantation than a conventional solid shank bone screw, less torque is required to implant the bone screw in a bone than is required by a conventional bone screw. Further, because them helical spikes 450 and 452 displace only a small amount of bone , the helical spikes do not create a core defect that could lead to bone deformation or failure, such as the helical spikes pulling out of the bone.

Advantageously, the conical shape of the helical spikes 450 and 452 increases the amount of surface area engaged by the bone screw 920, spreads any load on the bone screw out over different areas of the head 821 of the femur 812, and provides fixation over a larger volume of bone. These advantages of the conical shape of the helical spikes 450 and 452 are especially helpful when implanting the bone screw 920 in osteoporotic bone.

When implanted in the head 821 of the femur 812, the conical shape of the helical spikes 450 and 452 according to the tenth embodiment make the bone screw 920 highly resistant to being pulled out of the. femur and to toggling in the femur despite being subjected to substantial forces caused by human body movement and muscle memory. The use of a shape memory alloy for the helical spikes 450 and 452 allows the bone screw 920 to have a smaller diameter prior to implantation, which permits minimally invasive or endoscopic surgery through a cannula, and a wider diameter when implanted, which improves fixation in the femur. The bone screw 920 thus provides an effective means for compressing the fractured sections of bone together to prevent relative rotation of the fractured sections and permit healing of the fracture without causing further damage to the fractured sections.

In addition to the aforementioned advantages, the bone screws according to the present invention offer several other advantages to the clinician. The bone screws disclosed above can be used in metaphysical or apophyseal applications. Further, the disclosed bone screws are adaptable to a number of existing implant systems and provide maximum distal fixation for any type of anchorage device. The disclosed bone screws are applicable to a wide variety of fracture fixation applications, including but not limited to proximal femur/tibia fractures, proximal and distal humerus fractures, scapula/acromion fractures, and radius and/or ulna fractures.

From the above description of the invention, those skilled in the art will perceive improvements, changes and modifications. It should be understood that the present invention can be used for a variety of purposes and can be implanted in variety of different bones. Further, it is contemplated that the present invention could comprise a single helical spike or more than three spikes. Such improvements, changes and modifications within the skill of the art are intended to be covered by the appended claims.

Having described the invention, I claim:

1. An apparatus for attaching a first section of a bone to a second section of the bone, the second section being separated from the first section by a fracture of the bone, said apparatus comprising:

a bone screw having a platform for drivingly rotating said bone screw and at least two helical spikes for embedding into at least one of the first and second sections of the bone upon rotation of said platform, said platform having a first surface that is solid and that extends generally transverse to a longitudinal axis of said bone screw;

said at least two helical spikes projecting tangentially from said first surface of said platform and extending around said longitudinal axis, said at least two helical spikes having a tip portion at a distal end which penetrates into the bone as said platform is rotated;

said bone screw having a first condition in which a first portion of said bone screw is extendable into one of the first and second sections of the bone, said bone screw further having a second condition in which a second portion of said bone screw is extendable into the other of the first and second sections of the bone to bring the first and second sections into engagement with one another so that the fracture of the bone can heal;

said at least two helical spikes, when embedded into at least one of the first and second sections of the bone, being resistant to toggling in the bone and to being pulled axially from the bone.

2. The apparatus of claim 1 wherein the fracture of the bone is defined by a first edge on the first section of the bone and a second edge on the second section of the bone, the first and second edges being pressed into contact with each other as said bone screw is moved into said second condition.

3. The apparatus of claim 1 wherein in said first condition of said bone screw, said at least two helical spikes are for embedding into one of the first and second sections of the bone and, in said second condition of said bone screw, said at least two helical spikes are for embedding into both of the first and second sections of the bone.

4. The apparatus of claim 1 wherein each of said at least two helical spikes, when implanted, has a conical shape that increases in diameter as said at least two helical spikes extend away from said platform.

5. The apparatus of claim 1 wherein at least a portion of each of said at least two helical spikes is made of a shape memory alloy that is responsive to changes in temperature above and below a predetermined temperature transition range, said at least two helical spikes being heated above said predetermined temperature transition range as said at least two helical spikes are being implanted into the bone.

6. The apparatus of claim 5 further comprising a tubular sleeve for receiving said bone screw, said bone screw being positionable inside said tubular sleeve when the temperature of said at least two helical spikes is below said predetermined transition temperature range.

7. The apparatus of claim 6 wherein said tubular sleeve includes internal threads for mating with said at least two helical spikes and helping to draw said at least two helical spikes into said tubular sleeve as said platform is rotated.

8. The apparatus of claim 1 wherein each of said at least two helical spikes has a connecting portion at a proximal end connected to said platform and an intermediate portion extending between said connecting portion and said tip portion.

9. The apparatus of claim 8 comprising a pair of helical spikes extending around said longitudinal axis, said proximal ends of said pair of helical spikes being spaced 180° apart.

10. The apparatus of claim 8 comprising three helical spikes extending around said longitudinal axis, said proximal ends of said three helical spikes being spaced 120° apart.

11. The apparatus of claim 1 wherein said first surface has a shape that is complimentary to the shape of an outer surface of the bone for engaging the outer surface of the bone.

12. The apparatus of claim 1 wherein each of said at least two helical spikes has a solid cross-section.

13. The apparatus of claim 1 wherein each of said at least two helical spikes has a tubular cross-section.

14. The apparatus of claim 1 wherein a first portion of each of said at least two helical spikes has a solid cross-section and a second portion of each of said at least two helical spikes has a tubular cross-section.

15. The apparatus of claim 1 wherein said platform comprises a cylindrical body portion having oppositely disposed first and second ends, said at least two helical spikes projecting from said first end for embedding in the first section of the bone by rotation of said body portion, said first end of said body portion including a threaded section.

16. The apparatus of claim 15 further comprising a plate member having a sleeve section, said plate member for attaching to the second section of the bone, said sleeve section for extending through the second section of the bone and receiving said body portion of said bone screw.

17. The apparatus of claim 16 further comprising a fastener engaged with said threaded section of said body portion, wherein rotation of said fastener pulls said body portion of said bone screw farther into said sleeve section of said plate member to compress the first section of the bone against the second section of the bone.

18. The apparatus of claim 17 wherein said at least two helical spikes, when implanted, have a conical shape that increases in diameter as said at least two helical spikes extend away from said platform.

19. The apparatus of claim 18 wherein at least a portion of each of said at least two helical spikes is made of a shape memory alloy that is responsive to changes in temperature above and below a predetermined temperature transition range, said at least two helical spikes being heated above said predetermined temperature transition range as said at least two helical spikes are being implanted into the first section of the bone.

20. An apparatus for attaching a first section of a bone to a second section of the bone, the second section being separated from the first section by a fracture of the bone, said apparatus comprising:

a bone screw for extending between the first and second sections of the bone and for attaching the first section to the second section, said bone screw having a platform for drivingly rotating said bone screw, said platform including a first surface that is solid and that extends generally transverse to a longitudinal axis of said bone screw;

said bone screw further having at least two helical spikes for embedding into both of the first and second sections of the bone upon rotation of said platform, said at least two helical spikes projecting tangentially from said first surface of said platform and extending around said longitudinal axis, said at least two helical spikes having a tip portion at a distal end which penetrates into the bone as said platform is rotated;

said bone screw having a first condition in which said at least two helical spikes are embeddable into one of the first and second sections of the bone, said bone screw further having a second condition in which said at least two helical spikes are embeddable into both of the first and second sections of the bone to compress the first and second sections together so that the fracture of the bone can heal, said bone screw being movable from said first condition to said second condition by rotation of said platform;

said at least two helical spikes of said bone screw, when embedded into the first and second sections of the bone, being resistant to toggling in the bone and to being pulled axially from the bone.

21. The apparatus of claim 20 wherein each of said at least two helical spikes has a cylindrical shape with a generally constant overall diameter.

22. The apparatus of claim 20 wherein each of said at least two helical spikes, when implanted, has a conical shape that increases in diameter as said at least two helical spikes extend away from said platform.

23. The apparatus of claim 22 wherein at least a portion of each of said at least two helical spikes is made of a shape memory alloy that is responsive to changes in temperature above and below a predetermined temperature transition range, said at least two helical spikes being heated above said predetermined temperature transition range as said at least two helical spikes are being implanted into the bone.

24. The apparatus of claim 20 wherein each of said at least two helical spikes has a connecting portion at a proximal end connected to said platform and an intermediate portion extending between said connecting portion and said tip portion.

25. The apparatus of claim 24 comprising a pair of helical spikes extending around said longitudinal axis, said proximal ends of said pair of helical spikes being spaced 180° apart.

26. The apparatus of claim 24 comprising three helical spikes extending around said longitudinal axis, said proximal ends of said three helical spikes being spaced 120° apart.

27. The apparatus of claim 20 wherein said first surface has a shape that is complimentary to the shape of an outer surface of the bone for engaging the outer surface of the bone.

28. The apparatus of claim 27 wherein each of said at least two helical spikes has a solid cross-section.

29. The apparatus of claim 27 wherein each of said at least two helical spikes has a tubular cross-section.

30. The apparatus of claim 27 wherein a first portion of each of said at least two helical spikes has a solid cross-section and a second portion of each of said at least two helical spikes has a tubular cross-section.

* * * * *